US012678247B2

(12) United States Patent
Gao et al.

(10) Patent No.: US 12,678,247 B2
(45) Date of Patent: Jul. 14, 2026

(54) SURGICAL ROBOT, AND GRAPHICAL CONTROL DEVICE AND GRAPHICAL DISPLAY METHOD THEREOF

(71) Applicant: SHENZHEN EDGE MEDICAL CO., LTD., Guangdong (CN)

(72) Inventors: Yuanqian Gao, Guangdong (CN); Jianchen Wang, Guangdong (CN); Pai Wang, Guangdong (CN)

(73) Assignee: SHENZHEN EDGE MEDICAL CO., LTD., Shenzhen (CN)

( * ) Notice: Subject to any disclaimer, the term of this patent is extended or adjusted under 35 U.S.C. 154(b) by 477 days.

(21) Appl. No.: 18/030,675

(22) PCT Filed: Dec. 3, 2020

(86) PCT No.: PCT/CN2020/133487
§ 371 (c)(1),
(2) Date: Apr. 6, 2023

(87) PCT Pub. No.: WO2022/073289
PCT Pub. Date: Apr. 14, 2022

(65) Prior Publication Data
US 2023/0363841 A1     Nov. 16, 2023

(30) Foreign Application Priority Data
Oct. 8, 2020   (CN) .......................... 202011068074.0

(51) Int. Cl.
*A61B 34/37*          (2016.01)
*A61B 34/00*          (2016.01)
(Continued)

(52) U.S. Cl.
CPC .............. *A61B 34/37* (2016.02); *A61B 34/10* (2016.02); *A61B 34/25* (2016.02); *A61B 34/70* (2016.02);
(Continued)

(58) Field of Classification Search
CPC ......... A61B 34/37; A61B 34/10; A61B 34/25; A61B 34/70; A61B 34/30; A61B 34/76;
(Continued)

(56) References Cited

U.S. PATENT DOCUMENTS 6,424,885 B1 *   7/2002   Niemeyer .............. A61B 34/77
9,089,256 B2    7/2015   Tognaccini et al.
(Continued)

FOREIGN PATENT DOCUMENTS

CN        102448680 A      5/2012
CN        102802550 A      11/2012
(Continued)

OTHER PUBLICATIONS

International Search Report dated Jul. 7, 2021; International Application No. PCT/CN2020/133487; 3 pages (English translation).
(Continued)

*Primary Examiner* — Ellis B. Ramirez
(74) *Attorney, Agent, or Firm* — CANTOR COLBURN LLP

(57)          ABSTRACT

A surgical robot, a graphical control device and a graphical display method thereof, the surgical robot including: a display; at least two manipulators; and a controller configured to: when a first manipulator is detected to be in an operational mode, obtain state information of the joint assembly sensed by the sensors of the first manipulator; obtain a kinematic model of the first manipulator; acquire configuration parameters of a virtual camera; combine the configuration parameters of the virtual camera, the kinematic model of the first manipulator and the state information thereof so as to generate an image model of the first manipulator from a viewing point of the virtual camera; and display the image model of the first manipulator in a first display window of the display. The surgical robot facilitates
(Continued)

doctors observing the posture state of the manipulators that are used during a surgical process.

20 Claims, 16 Drawing Sheets

(51) Int. Cl.
 *A61B 34/10* (2016.01)
 *B25J 9/16* (2006.01)

(52) U.S. Cl.
 CPC ....... *A61B 2034/102* (2016.02); *B25J 9/1605* (2013.01)

(58) Field of Classification Search
 CPC .............. A61B 34/35; A61B 2034/102; A61B 2034/301; A61B 90/36; A61B 2090/064; A61B 2090/365; A61B 2562/0247; A61B 2562/0257; B25J 9/1605; B25J 9/0087; B25J 9/1689; G06T 19/20; G06T 19/003; G06T 19/006; G06T 2210/41; G06T 2219/2016; G06T 7/70; G05B 2219/40479; G05B 2219/45118
 USPC .................. 700/255, 245, 246, 264; 901/47; 601/137
 See application file for complete search history.

(56) References Cited

U.S. PATENT DOCUMENTS

| | | | |
|---|---|---|---|
| 9,717,563 | B2 | 8/2017 | Tognaccini et al. |
| 9,789,608 | B2 | 10/2017 | Itkowitz et al. |
| 10,137,575 | B2 | 11/2018 | Itkowitz et al. |
| 10,258,425 | B2 | 4/2019 | Mustufa et al. |
| 10,368,952 | B2 | 8/2019 | Tognaccini et al. |
| 10,820,949 | B2 | 11/2020 | Prisco et al. |
| 11,382,702 | B2 | 7/2022 | Tognaccini et al. |
| 2002/0082612 | A1 | 6/2002 | Moll et al. |
| 2008/0180392 | A1* | 7/2008 | Kishi ..................... A61B 34/37 |
| 2009/0062813 | A1 | 3/2009 | Prisco et al. |
| 2009/0192524 | A1 | 7/2009 | Itkowitz et al. |
| 2009/0326318 | A1 | 12/2009 | Tognaccini et al. |
| 2009/0326553 | A1 | 12/2009 | Mustufa et al. |
| 2015/0366625 | A1 | 12/2015 | Tognaccini et al. |
| 2017/0265948 | A1 | 9/2017 | Prisco et al. |
| 2017/0282372 | A1 | 10/2017 | Itkowitz et al. |
| 2017/0304012 | A1 | 10/2017 | Tognaccini et al. |
| 2018/0126559 | A9 | 5/2018 | Itkowitz et al. |
| 2019/0005848 | A1* | 1/2019 | Garcia Kilroy ........ G16H 40/67 |
| 2019/0047154 | A1 | 2/2019 | Itkowitz et al. |
| 2019/0151032 | A1* | 5/2019 | Mustufa ................... G06T 3/60 |
| 2019/0209262 | A1 | 7/2019 | Mustufa et al. |
| 2019/0298463 | A1 | 10/2019 | Tognaccini et al. |
| 2020/0237456 | A1 | 7/2020 | Prisco et al. |
| 2022/0096163 | A1* | 3/2022 | Payyavula ............. G16H 40/67 |
| 2023/0270510 | A1* | 8/2023 | Diolaiti .................. A61B 34/37 |
| 2023/0293252 | A1* | 9/2023 | Xu .......................... A61B 34/37 |

FOREIGN PATENT DOCUMENTS

| | | |
|---|---|---|
| CN | 102814815 A | 12/2012 |
| CN | 104363850 A | 2/2015 |
| CN | 105188590 A | 12/2015 |
| CN | 105748026 A | 7/2016 |
| CN | 107530130 A | 1/2018 |
| CN | 108527305 A | 9/2018 |
| CN | 109109018 A | 1/2019 |
| CN | 109275333 A | 1/2019 |
| EP | 3115159 A1 | 1/2017 |
| WO | 2009158164 A1 | 12/2009 |
| WO | 2010151438 A1 | 12/2010 |
| WO | 2018013198 A1 | 1/2018 |

OTHER PUBLICATIONS

International Search Report dated Jul. 7, 2021; International Application No. PCT/CN2020/133487; 5 pages (non- English).
Written Opinion dated Jul. 7, 2021; International Application No. PCT/CN2020/133487; 4 pages (non-English).
Chinese First Office Action corresponding to CN Application No. 2020110680740; Issue Date, Jun. 11, 2021, 3 pages.
Chinese Notice of Allowance corresponding to CN Application No. 2020110680740; Issue Date, Jan. 24, 2022, 3 pages.
Extended European Search Report corresponding to EP Application No. 20956604.1; Mailing Date, Aug. 28, 2024, 7 pages.

* cited by examiner 1        2    3        4

1        2    3        4

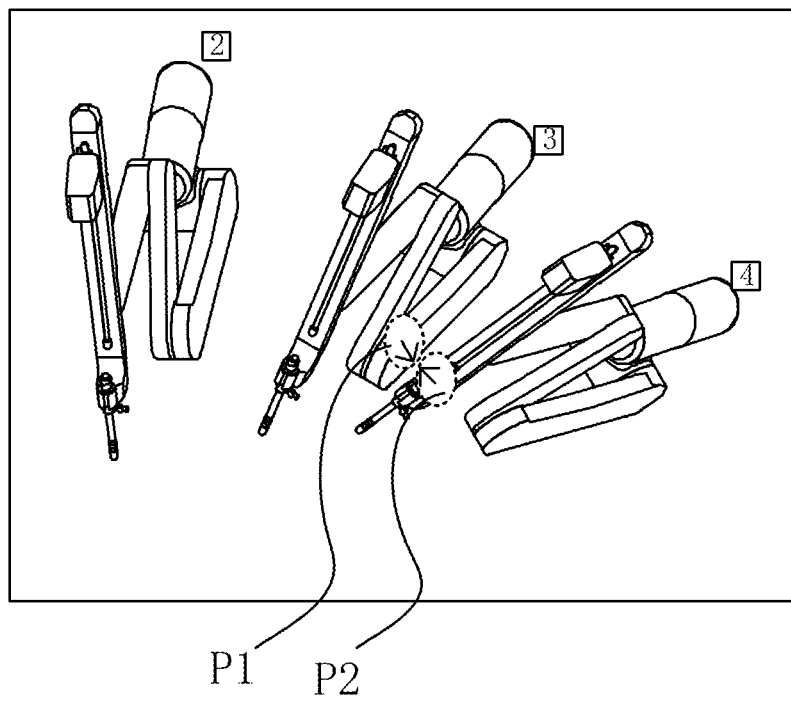

P1  P2

FIG. 20 building a geometric model of the third manipulator based on a kinematic model and structural features of the third manipulator, and building a geometric model of the fourth manipulator based on a kinematic model and structural features of the fourth manipulator — S7211 obtaining a point set of external information in a reference frame by discretizing the geometric model of the third manipulator, and obtaining a point set of external information in the reference frame by discretizing the geometric model of the fourth manipulator — S7212 determining the minimum distance between the third manipulator and the fourth manipulator based on the point sets of external information of the third manipulator and the fourth manipulator — S7213

FIG. 21

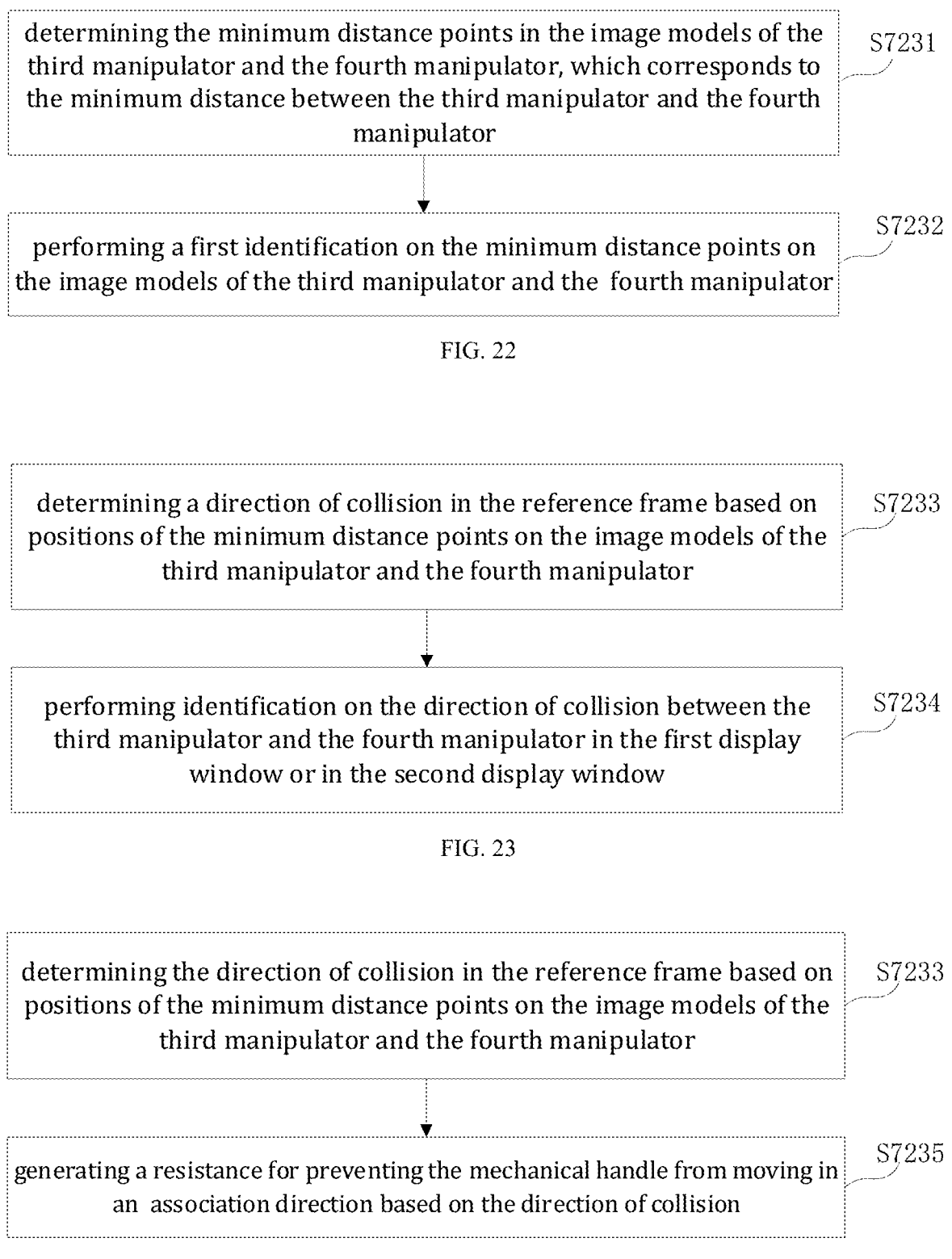

determining the minimum distance points in the image models of the third manipulator and the fourth manipulator, which corresponds to the minimum distance between the third manipulator and the fourth manipulator

S7231 performing a first identification on the minimum distance points on the image models of the third manipulator and the fourth manipulator

S7232

FIG. 22 determining a direction of collision in the reference frame based on positions of the minimum distance points on the image models of the third manipulator and the fourth manipulator

S7233 performing identification on the direction of collision between the third manipulator and the fourth manipulator in the first display window or in the second display window

S7234

FIG. 23 determining the direction of collision in the reference frame based on positions of the minimum distance points on the image models of the third manipulator and the fourth manipulator

S7233 generating a resistance for preventing the mechanical handle from moving in an association direction based on the direction of collision

SURGICAL ROBOT, AND GRAPHICAL CONTROL DEVICE AND GRAPHICAL DISPLAY METHOD THEREOF

CROSS-REFERENCE TO RELATED APPLICATIONS

The present disclosure is a 35 U.S.C. § 371 national stage application of PCT application No. PCT/CN2020/133487, filed on Dec. 3, 2020, which claims the benefit of Chinese Patent Application NO. 202011068074.0, entitled "surgical robot, and graphical control device and graphical display method thereof", which was filed with China National Intellectual Property Administration on Oct. 8, 2020, and the entire contents each of which are incorporated herein by reference thereto.

FIELD

The present disclosure relates to medical instruments, more particularly to a surgical robot, and a graphical control device and a graphical display method thereof.

BACKGROUND

Minimally invasive surgery refers to a surgical method for performing surgery in a human body cavity using modern medical instruments such as laparoscopes, thoracoscopes, and related devices. Compared with traditional surgery modes, minimally invasive surgery has advantages of resulting in small trauma, light pain, fast recovery, and etc.

With advances in science and technology, minimally invasive surgical robotics are increasingly mature and widely used. In a surgical robot performing tiny holes minimally invasive surgery, which surgical robot generally includes a master control console and a slave operating device, the slave operating device includes a plurality of manipulators, each for holding an operating arm with an end effector. The end effector includes an image end effector and an operation end effector. The master control console includes a display and a handle. By operating the handle to conduct a remote surgery, a doctor controls the movement of a corresponding manipulator and its related operating arm in the field of view provided by the image end effector and displayed on the display.

Because of the structure features of the operating arm of the surgical robot performing tiny holes minimally invasive surgery, i.e. at most three DoFs perturbing the poses, one open/close-related DoF and no position-related DoF, the doctor may easily observe or predict the poses between the operating arms by observing the field of view displayed on the display but he/she is not able to observe or predict the poses of the manipulator. This may easily have an adverse effect to the remote surgery, for example, a medical accident may be caused due to a collision between the manipulators, for another example, the fluency of the surgery may be affected because the doctor has to frequently interrupt the operation process and observe the manipulators from outside of the display.

SUMMARY

In view of the above, the present disclosure provides a surgical robot, and a graphical control device and a graphical display method thereof, which facilitates a doctor to observe the pose of the manipulator used during a surgical process.

A first aspect of the present disclosure provides a surgical robot, including: a display; at least two manipulators, each including a plurality of joint assemblies, each joint assembly being provided with a sensor configured to sense a state of the joint assembly; and a controller, coupled to the display and to the sensor, and configured for: when a first manipulator is detected to be in an operational mode, obtaining state information of the joint assemblies sensed by the sensors of the first manipulator; obtaining a kinematic model of the first manipulator; obtaining configuration parameters of a virtual camera; generating an image model of the first manipulator from a viewing point of the virtual camera by combining the configuration parameters of the virtual camera, the kinematic model of the first manipulator, and the state information of the first manipulator; and displaying the image model of the first manipulator in a first display window of the display.

In one embodiment, when a second manipulator is detected to be in an idle mode, obtaining state information of the joint assemblies sensed by the sensors of the second manipulator; obtaining a kinematic model of the second manipulator; generating an image model of the second manipulator from the viewing point of the virtual camera by combining the configuration parameters of the virtual camera, the kinematic model of the second manipulator and the state information of the second manipulator; and displaying the image model of the second manipulator in the first display window of the display, or displaying the image models of the first manipulator and of the second manipulator in a second display window of the display.

In one embodiment, the controller is configured for: when generating the image model of the second manipulator from the viewing point of the virtual camera by combining the configuration parameters of the virtual camera and the kinematic model of the second manipulator, generating the image model of the second manipulator from the viewing point of the virtual camera by combining the configuration parameters of the virtual camera, the kinematic model of the second manipulator and the state information of the second manipulator after determining a possibility of collision between the first manipulator and the second manipulator.

In one embodiment, the controller is configured for executing following steps to determine whether there is a possibility of collision between the first manipulator and the second manipulator: calculating a reachable workspace of the first manipulator; determining whether the reachable workspace of the first manipulator covers at least part of the second manipulator; determining that there is possibility of collision between the first manipulator and the second manipulator, if it is determined that the reachable workspace of the first manipulator covers at least part of the second manipulator.

In one embodiment, the controller is configured for: differently identifying the image model of the first manipulator and the image model of the second manipulator in the first display window or in the second display window.

In one embodiment, the controller is configured for: hiding or displaying an image model of any one of the manipulators in the first display window or in the second display window according to an instruction.

In one embodiment, the controller is configured for: calculating a reachable workspace of the first manipulator; generating an image model of the reachable workspace of the first manipulator from the viewing point of the virtual camera by combining the configuration parameters of the virtual camera and the reachable workspace of the first manipulator; displaying the image model of the reachable workspace in the first display window or in the second display window.

In one embodiment, the image model of the reachable workspace is a computer model or a projective model.

In one embodiment, an origin of the image model of the reachable workspace is coincident with a motion center of the first manipulator.

In one embodiment, the origin of the image model of the reachable workspace is positioned on an axis of the joint assembly at a proximal end of the first manipulator.

In one embodiment, the first manipulator is configured to include a safe motion space within the reachable workspace, the controller is configured for: generating an image model of the safe motion space of the first manipulator by combining the configuration parameters of the virtual camera and the safe motion space of the first manipulator from the viewing point of the virtual camera; displaying the image model of the safe motion space in the first display window or in the second display window.

In one embodiment, the controller is configured for: generating an identifier to identify the image model of the first manipulator, the safe motion space, and/or the reachable workspace in the first display window or in the second display window when the image model of the first manipulator is detected to have moved from the image model of the safe motion space to a part of the image model of the reachable workspace other than the safe motion space.

In one embodiment, the controller is configured for: generating an identifier to identify at least one part of an image model of a third manipulator from the manipulators in the first display window or in the second display window when the third manipulator is detected to have reached a threshold of event.

In one embodiment, the threshold is a warning threshold, the event is a situation to be avoided.

In one embodiment, the warning threshold is based on a distance between the third manipulator and a fourth manipulator from the manipulators, the situation to be avoided is a collision between the third manipulator and the fourth manipulator.

In one embodiment, the controller is configured for: obtaining a minimum distance between the third manipulator and the fourth manipulator, and determining a relationship between the minimum distance and the warning threshold; generating a first identifier to identify minimum distance points on the image models of the third manipulator and the fourth manipulator in the first display window or in the second display window when the minimum distance has reached the warning threshold, but not reached a threshold corresponding to the situation to be avoided.

In one embodiment, the controller is configured for: generating a second identifier to identify the minimum distance points on the image models of the one third manipulator and the fourth manipulator in the first display window or in the second display window when the minimum distance has reached the threshold corresponding to the situation to be avoided.

In one embodiment, the controller is configured for: obtaining the minimum distance between the third manipulator and the fourth manipulator, and determining the relationship between the minimum distance and the warning threshold, which includes: building a geometric model of the third manipulator based on a kinematic model and structural features of the third manipulator, and building a geometric model of the fourth manipulator based on a kinematic model and structural features of the fourth manipulator; obtaining a point set of external information of the third manipulator by discretizing the geometric model of the third manipulator in a reference frame, and obtaining a point set of external information of the fourth manipulator by discretizing the geometric model of the fourth manipulator in the reference frame; and determining the minimum distance between the third manipulator and the fourth manipulator based on the point sets of external information of the third manipulator and of the fourth manipulator; and generating the first identifier to identify the minimum distance points on the image models of the third manipulator and the fourth manipulator in the first display window or in the second display window, which includes: determining the minimum distance points corresponding to the minimum distance, and generating the first identifier to identify the minimum distance points on the image models of the third manipulator and the fourth manipulator in the first display window or in the second display window.

In one embodiment, the controller is configured for: determining a direction of collision based on positions of the minimum distance points on the image models of the third manipulator and the fourth manipulator in the reference frame when the minimum distance has reached to the warning threshold; and generating an identifier to identify the direction of collision between the a third manipulator and the fourth manipulator in the first display window or in the second display window.

In one embodiment, the surgical robot includes a mechanical handle coupled to the controller and configured to control the manipulators to move, the controller is configured for: generating a resistance to prevent the mechanical handle from moving in an association direction based on the direction of collision.

In one embodiment, the mechanical handle includes a plurality of joint assemblies and drive motors for actuating each of the joint assemblies to move, each of the drive motors are coupled to the controller, the controller is configured for: causing a drive motor in the association direction to generate a reverse torque based on the resistance.

In one embodiment, the controller is configured for: magnitude of the reverse torque is set to be negatively correlated with the minimum distance when the minimum distance is between the warning threshold and the threshold corresponding to the situation to be avoided.

In one embodiment, the warning threshold is based on a range of motion of at least one joint assembly of the third manipulator, the situation to be avoided is a limitation of the range of motion of the at least one joint assembly of the third manipulator.

In one embodiment, the controller is configured for: performing identification on the first manipulator in the first display window or in the second display window.

In one embodiment, the controller is configured for: generating an identifier to identify an image model of a third manipulator from the first manipulator in the first display window or in the second display window when a movement of the third manipulator is detected.

In one embodiment, the image model of the first manipulator is a computer model or a projective model presenting structural features of the first manipulator.

In one embodiment, the operating arm includes a plurality of joint assemblies and sensors configured to sense the state of the joint assemblies; the controller is configured for: obtaining state information of the joint assemblies sensed by the sensors of the operating arm on the first manipulator; obtaining a kinematic model of the operating arm based on the state information of the operating arm; generating an image model of the operating arm from the viewing point of the virtual camera by combining the configuration parameters of the virtual camera and the kinematic model of the operating arm; and displaying the image model of the operating arm in the first display window of the display, or displaying the image model of the first manipulator and the image model of the operating arm in a second display window of the display.

In one embodiment, the controller is configured for: hiding or displaying an image model of any part of a first manipulator assembly consisting of the first manipulator and the operating arm thereon in the first display window or in the second display window according to an instruction.

In one embodiment, the surgical robot further includes an input device coupled to the controller and configured to set the configuration parameters of the virtual camera.

In one embodiment, the configuration parameters include a pose of the virtual camera in a reference frame.

In one embodiment, the configuration parameters include virtual field angle of the virtual camera, and/or a virtual depth of field of the virtual camera; or, the configuration parameters include a virtual focal length of the virtual camera, and/or a virtual aperture of the virtual camera.

In one embodiment, the controller is configured for: calculating a reachable workspace of the first manipulator; determining a union space of the reachable workspace of the first manipulator; and controlling the virtual camera to keep facing the union space based on the union space.

In one embodiment, the controller is configured for: determining a center of the union space while determining the union space of the reachable workspace of the first manipulator; controlling an optical axis of the virtual camera to keep intersecting on the center of the union space based on the center of union space while controlling the virtual camera to keep facing the union space based on the union space.

Another aspect of the present disclosure provides a graphical display method of a surgical robot, the surgical robot includes: a display; and at least two manipulators, each including a plurality of joint assemblies, each joint assembly being provided with a sensor configured to sense a state of the joint assembly; the graphical display method includes: when a first manipulator is detected to be in an operational mode, obtaining state information of the joint assemblies sensed by the sensors of the first manipulator; obtaining a kinematic model of the first manipulator; obtaining configuration parameters of a virtual camera; generating an image model of the first manipulator from a viewing point of the virtual camera by combining the configuration parameters of the virtual camera, the kinematic model of the first manipulator, and the state information of the first manipulator; and displaying the image model of the first manipulator in a first display window of the display.

A further aspect of the present disclosure provides a computer-readable storage medium, the computer-readable storage medium storing computer programs, the computer programs is configured for loading and executing procedures of the graphical display method according to any embodiment as above by a processing unit.

A further aspect of the present disclosure provides a graphical display device of a surgical robot, including: a memory, configured for storing computer programs; and a processing unit, configured for loading and executing the computer programs; the computer programs configured for loading and executing procedures of the graphical display method according to any embodiment as above by a processing unit.

The surgical robot, and the graphical control device and the graphical display method thereof of the present disclosure includes the following beneficial effects:

By observing the first manipulator positioned outside of the patient's body with the virtual camera, generating the image model of the first manipulator from the viewing point of the virtual camera, and displaying the image model of the first manipulator in the first display window of the display, the present disclosure in one aspect may help doctors to observe the poses of the first manipulator to facilitate surgery, and in another aspect may save the cost required for setting a real camera.

BRIEF DESCRIPTION OF THE DRAWINGS

FIG. 19 to FIG. 20 are graphic interfaces of the operation state shown in FIG. 19 according to different embodiments;

FIG. 21 to FIG. 26 are flow diagrams of the graphical display method of the surgical robot according to different embodiments of the present disclosure.

DETAILED DESCRIPTION OF THE EMBODIMENTS

Figure 1:
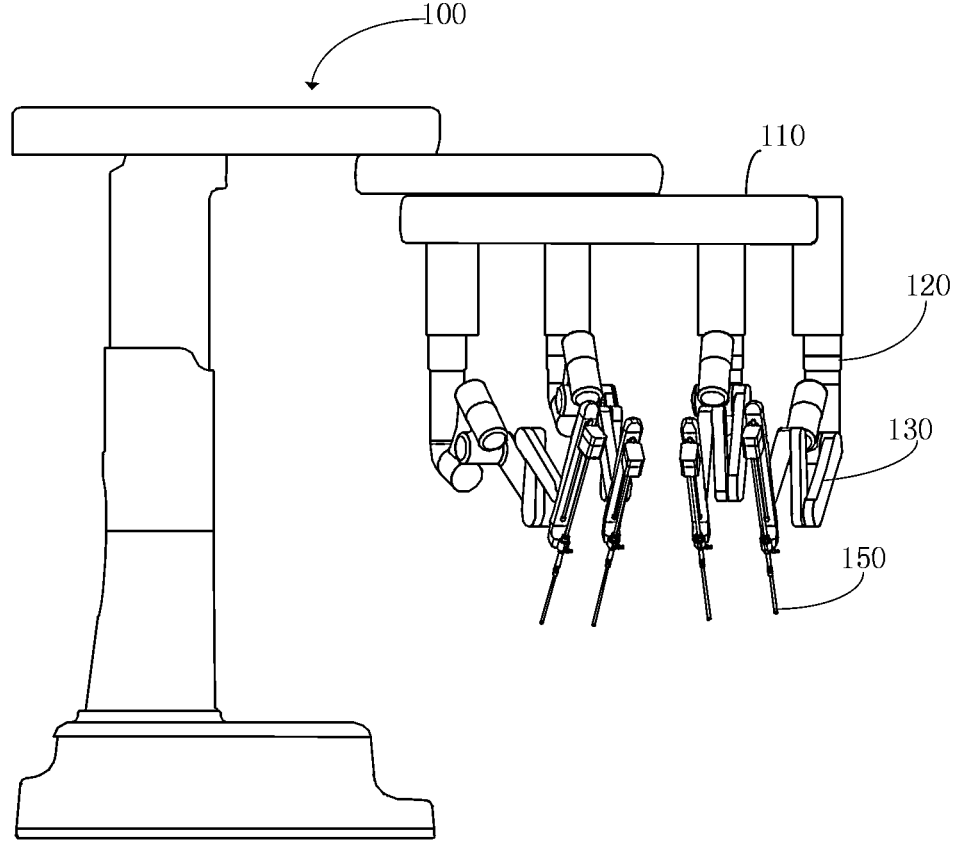
FIG. 1 is a schematic structure diagram of a slave operating device of a surgical robot according to an embodiment of the present disclosure.
Figure 2:
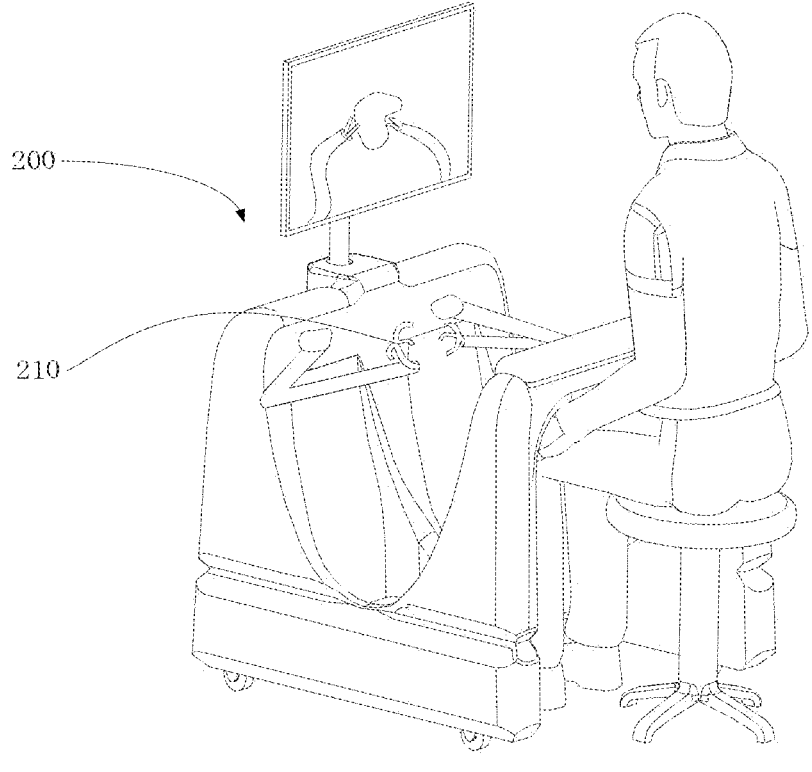
FIG. 2 is a schematic structure diagram of a master operating device of the surgical robot according to an embodiment of the present disclosure.
Figure 3:
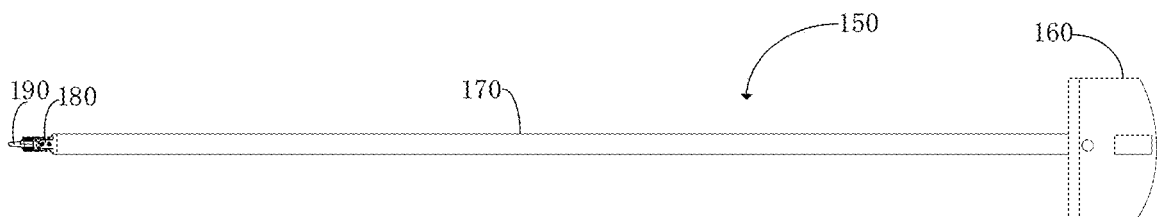
FIG. 3 is a schematic structure diagram of a manipulator of the slave operating device according to an embodiment of the present disclosure.
Figure 4:
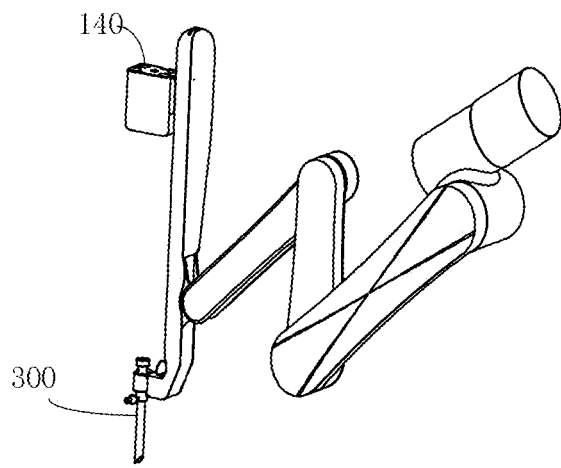
FIG. 4 is a schematic structure diagram of an operating arm according to an embodiment of the present disclosure.

Implementations of the disclosure will now be described, by way of embodiments only, with reference to the drawings. The disclosure is illustrative only, and changes may be made in the detail within the principles of the present disclosure. It will, therefore, be appreciated that the embodiments may be modified within the scope of the claims.

It should be noted that when an element is referred to as being "disposed on" another element, it may be directly on the other element or intervening elements may also be present. When an element is considered to be "connected" to another element, it may be directly connected to another element or intervening elements may be present at the same time. When an element is considered to be "coupled" to another element, it may be directly coupled to another element or intervening elements may be present at the same time. As used herein, the terms "vertical", "horizontal", "left", "right" and the like are intended for purposes of illustration only and are not intended to be limiting. As used herein, the terms "distal end" and "proximal end" are common terms in the art of interventional medical devices, where "distal end" refers to the end far away from the operator during the surgical procedure, and the "proximal end" refers to the end close to the operator during the surgical procedure. Unless defined otherwise, all technical and scientific terms used herein have the same meaning as commonly understood by one of ordinary skill in the art. The terminology used herein is for the purpose of describing particular embodiments only and is not intended to be limiting of the invention. As used herein, the term "and/or" includes all combinations of one or more of the associated listed items. As used herein, the terms "first/second" and the like represent one component and a class of two or more components having common features.

Unless defined otherwise, all technical and scientific terms used herein have the same meaning as commonly understood by one of ordinary skill in the art. The terminology used herein is for the purpose of describing particular embodiments only and is not intended to be limiting of the invention. As used herein, the term "and/or" includes all combinations of one or more of the associated listed items.

Referring to FIG. 1 to FIG. 4, schematic structure diagrams of a surgical robot according to an embodiment and partial schematic diagrams thereof are illustrated.

A surgical robot includes a slave operating device 100 and a master control console 200 controlling the slave operating device 100.

The slave operating device 100 includes a main arm 110, an adjusting arm 120, and a manipulator 130, which are sequentially connected. The number of the adjusting arm 120 may be two or more, for example, may be four, and the number of the manipulator 130 may be two or more, for example, may be four. The distal end of the main arm 110 includes an orienting platform, the proximal end of each of the adjusting arms 120 is connected to the orienting platform, and the proximal end of each of the manipulators 130 is connected to the distal end of each of the adjusting arms 120. The manipulator 130 may be configured to be detachably connected to an operating arm 150, the manipulator 130 includes a plurality of joint assemblies. The operating arm 150 includes an actuating device 160, a link 170, a connecting assembly 180, and an end effector 190, which are sequentially connected. The joint assemblies may include the link 170 and the connecting assembly 180, or may include only the connecting assembly 180. The link 170 may be a hollow structure for actuating cables to pass through. The actuating device 160 may actuate the end effector 190 to move by manipulating the joint assemblies with the actuating cables. The end effector 190 includes an image end effector 190 and an operation end effector 190.

During a surgical process, the manipulator 130 may be positioned outside the patient's body, the distal end of the operating arm 150 may insert into the patient's body with a puncture device 300 mounted to the manipulator 130. The doctor may control the manipulator 130 and the operating arm 150 to move coordinatively so as to adjust the pose of the end effector 190. The joint assemblies of the manipulator 130 may be mainly configured for positioning, the joint assemblies of the operating arm 150 may be mainly configured for orientation. The manipulator 130 may adjust the position and the pose of the end effector 190 by manipulating the operating arm 150 to move.

The master control console 200 includes a handle 210 and a display. The doctor may send control instructions to the slave operating device 100 by operating the handle 210, so as to cause the slave operating device 100 to perform operations in response to the control instructions, and the doctor may observe the surgical site captured by the image end effector 190 on the display.

Figure 5:
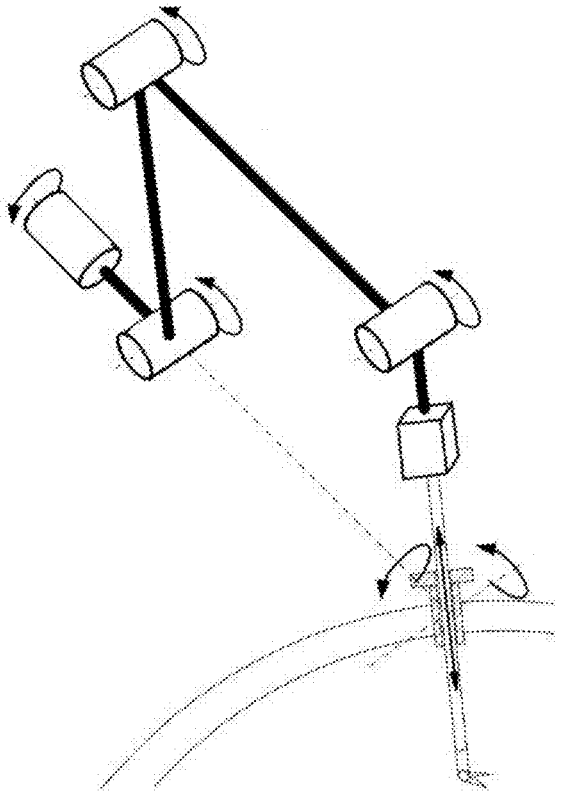
FIG. 5 is a principal structure diagram of the manipulator shown in FIG. 4.

Referring to FIG. 5, the manipulator 130 includes two rotary joint assemblies and one prismatic joint assembly. The second rotary joint assembly from the rotary joint assemblies may actuate a parallelogram-based remote center of motion mechanism to transfer a rotation to the remote center, so as to realize the axes of three DoFs (degrees of freedom) to intersect at a point (i.e., the remote center) in space. The prismatic joint assembly may be located at the distal end of the manipulator 130. The prismatic joint assembly includes an actuating device 140, and the actuating device 140 of the prismatic joint assembly may engage with the actuating device 160 of the operating arm 150, so as to allow the transfer of the actuating force.

Figure 6:
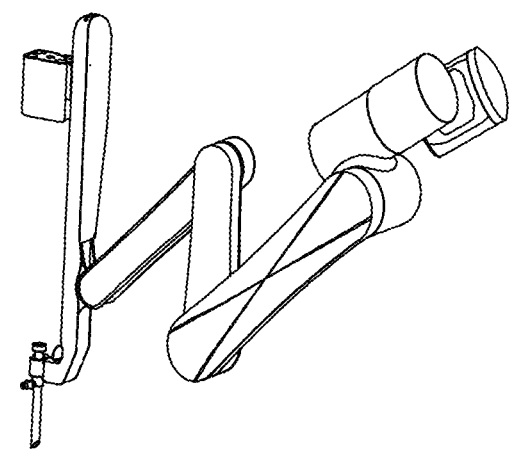
FIG. 6 is a schematic structure diagram of a manipulator of a slave operating device according to another embodiment of the present disclosure.
Figure 7:
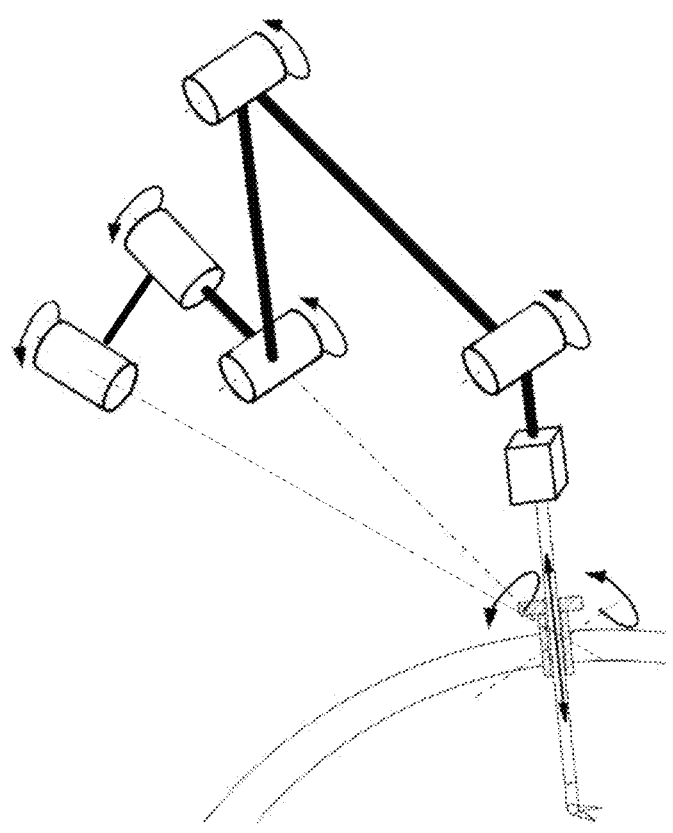
FIG. 7 is a principal structure diagram of the manipulator shown in FIG. 6.

In some embodiments, please refer to FIGS. 6 and 7 in combination, an additional rotary joint assembly may be arranged at the proximal end of the first rotary joint assembly, so as to increase the range of motion of the manipulator 130. The axis of the rotary joint assembly may intersect at the remote center but not coincident with the axis of the first rotary joint assembly, so as to ensure the distal end of the manipulator 130 may still rotate around the remote center.

The operating arm 150 includes three rotary joint assemblies, for example, the link 170 may roll with respect to the actuating device 160, and the connecting assembly 180 may yaw and pitch with respect to the link 170. For another example, the link 170 may be fixed with respect to the actuating device 160, and roll, yaw and pitch with respect to the link 170 through the connecting assembly 180. Thereby the three basic DoFs of a wrist, i.e., the yaw, the pitch, and the roll, can be realized. The three DoFs of a wrist may be mainly configured for orientation, since the three DoFs have little perturbation to the position. The connecting assembly 180 may further have an open/close-related DoF to actuate the end effector 190 to open and close.

The manipulator 130 and the operating arm 150 thereon may move coordinately, that is, they may move with six DoFs (three position-related DoFs and three pose-related DoFs) to satisfy the needs of the surgery.

The surgical robot may further include a controller. The controller may be integrated in the master control console 200 or integrated in the slave operating device 100. Or, the controller may be independent from the master control console 200 and the slave operating device 100, for example, the controller may be deployed locally, or deployed in the cloud. The controller may include at least one processor.

In some embodiments, each of the joint assemblies of the manipulator and the operating arm of the slave operating device 200 includes a sensor configured to sense the state of the joints. The sensors include angle sensors and displacement sensors, the angle sensors are configured to sense the rotational motion of the joint assemblies, and the displacement sensors are configured to sense the linear motion of the joint assemblies. Specifically, appropriate sensors can be configured according to the type of the joint assemblies. The controller may couple to the sensors and to the display of the master control console.

Figure 8:
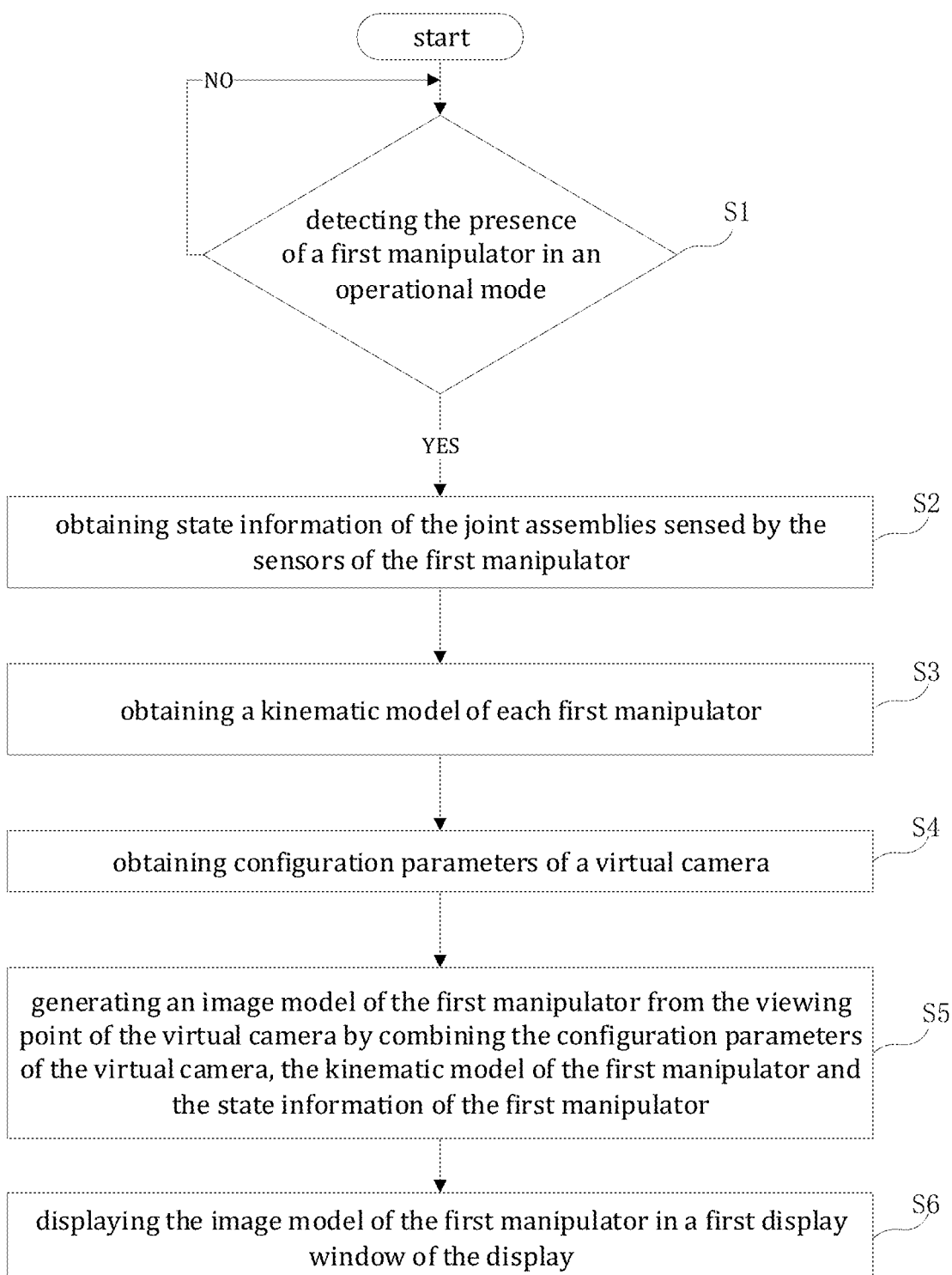
FIG. 8 is a flow diagram of a graphical display method of a surgical robot according to an embodiment of the present disclosure.

In some embodiments, a graphical display method of the surgical robot is provided, which can be executed by the controller mentioned above. Referring to FIG. 8, the graphical display method includes the following steps:

Step S1, detecting the presence of a first manipulator from a plurality of manipulators which is in an operational mode.

The manipulator being in the operational mode may be simply understood as that the manipulator is provided with an operating arm, and more precisely, be understood as that the manipulator is provided with the operating arm and the operating arm is inserted into the patient's body by the guiding and the sealing of a puncture device 300. Generally, the operating arm mounted to the manipulator may be inserted into the patient's body through the puncture device 300, and a manipulator without an operating arm may be located at a relatively distant position when the doctor arranges the operation, so that the manipulator being in the operational mode can be simply regarded as the manipulator being provided with the operating arm. Opposite to the concept of the operational mode, there is an idle mode for the manipulator, and the manipulator without the operating arm can be regarded as that the manipulator is in the idle mode. Generally, the manipulator in the idle mode may be in a static state. Herein, the first manipulator generally refers to a type of manipulator, and should not be understood as that it only refers to a specific manipulator, and it may represent at least one manipulator.

A detection device can be provided to each of the manipulator, which is configured to detect whether an operating arm is mounted thereon. For example, the detection device may include a proximity sensor, a pressure sensor or a photoelectric sensor, etc. In other embodiments, whether the manipulator is in the operational mode may be determined by the manual input from the doctor, in this way, the manipulator can be set to be in the operational mode even if the manipulator is not provided with an operating arm.

Also, a memory can be provided to the operating arm to store the basic information of the operating arm, such as the link parameters and the types of e the operating arm, etc. And another detection device can be provided to the manipulator to read the basic information of the operating arm.

Proceed to step S2 if the presence of the first manipulator is detected in Step S1. Otherwise, continue with Step S1.

Step S2, obtaining the state information of the joint assemblies sensed by the sensors of the first manipulator.

The sensed state information of the joint assemblies includes angle information and/or displacement information.

Step S3, obtaining a kinematic model of the first manipulator.

For example, the kinematic model can be pre-built. For another example, the kinematic model can be built in real time, such as by combining the state information of the first manipulator and the link parameters and using forward kinematics to obtain the kinematic model in the reference frame For example, the reference frame may be the base coordinate system of the proximal end of the main arm, or may be the tool coordinate system of the distal end of the main arm (i.e., the tool coordinate system of the orienting platform).

Step S4, obtaining configuration parameters of a virtual camera.

As its name implies, the virtual camera may be a camera that does not actual exist. The virtual camera does not actually capture the images of the objects, and only represents a concept about at least one viewing point. Even so, it is still possible to set the parameters of the virtual camera.

It is possible to configure parameters of the virtual camera. The parameters (i.e., the configuration parameters) of the virtual camera may at least include (virtual) poses, camera parameters corresponding to those of an actual camera such as the focal length and/or the aperture, the virtual camera parameters may also include the virtual focal length and/or the virtual aperture. Generally, the (virtual) focal length may correspondingly adjust the field angle of the (virtual) camera, and the (virtual) aperture may correspondingly adjust the depth of the field. In some embodiments, it is also possible to describe the virtual camera parameters including the field angle and the depth of the field. With respect to the virtual camera, the field angle and/or the depth of the field are virtual. Even if the focal length and the aperture of the camera are virtual, it is also possible to combine, for example the same imaging principle of the actual camera, to realize the purpose of the present disclosure. Different virtual camera parameters can realize different imaging effects.

The virtual camera parameters can be stored in the system configuration files of the memory of the surgical robot, and obtained by reading the system configuration files. The virtual camera parameters may also be manually set by the doctor before the operation process or during the operation process as needed through an input device coupled to the controller. such setting is on demand, for example, the virtual camera parameters can be obtained by inputting relative data(s) into a text control, and for example, the virtual camera parameters can be obtained by selecting from a tab control.

The pose of the virtual camera can be the same as the pose of the actual camera (i.e., the image end effector), so as to observe the operating arm from the same viewing point as the actual camera. The pose of the virtual camera also can be different from the pose of the actual camera, so as to observe the operating arm from a different viewing point from the actual camera. Generally, it is possible to select the pose of the virtual camera different from that of the pose the actual camera to observe, this may help obtain more comprehensive information of the operating arm. For example, the operating arm also can be a camera arm, and observations can be made through the virtual camera.

Step S5, generating an image model of the first manipulator from the viewing point of the virtual camera by combining the configuration parameters of the virtual camera, the kinematic model of the first manipulator and the state information of each joint assembly of the first manipulator.

For example, the image model of the first manipulator can be a computer model substantially embodying the structural features of the first manipulator. And for another example, the image model of the first manipulator can be a projective model substantially embodying the feature point projections of the first manipulator. Each of the two image models of the first manipulator can display the image model from the viewing point of the virtual camera, each of the two image models can present an effect of a plane graph and can follow the movement of the first manipulator to present a dynamic effect.

Step S6, displaying the image model of the first manipulator in a first display window of the display.

Since the display also displays the actual image of the lesion captured by the image end effector, the first display window can be arranged at an edge area, such as the bottom, the sides, and/or the top, of the display in order not to affect the operation However, it is also possible to arrange the first display window at the center area of the display if necessary. The image model of the first manipulator displayed on the first display window may be generated as a perspective image model in order to not prevent the doctor from observing the actual image of the focus.

By observing the first manipulator positioned outside the patient's body through the virtual camera, generating the image model of the first manipulator from the viewing point of the virtual camera, and displaying the image model of the first manipulator in the first display window of the display, the above steps S1-S6 in one aspect can help the doctor to observe the pose of the first manipulator to facilitate performing surgery, for example, it can avoid the collisions between the first manipulators, in another aspect, the steps save the cost required for setting an actual camera, in a further aspect, the steps eliminate the interference of the unnecessary images caused by the actual camera, in a further aspect, the steps realize the observation of the first manipulator having the operating arm with the image end effector.

Figure 9:
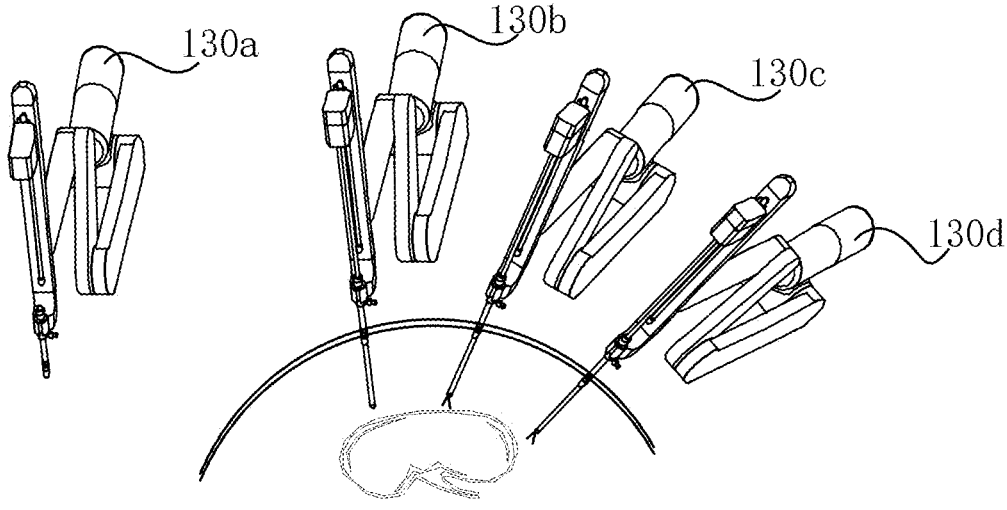
FIG. 9 is a partial schematic diagram of an operation state of the surgical robot according to an embodiment of the present disclosure.
Figure 10:
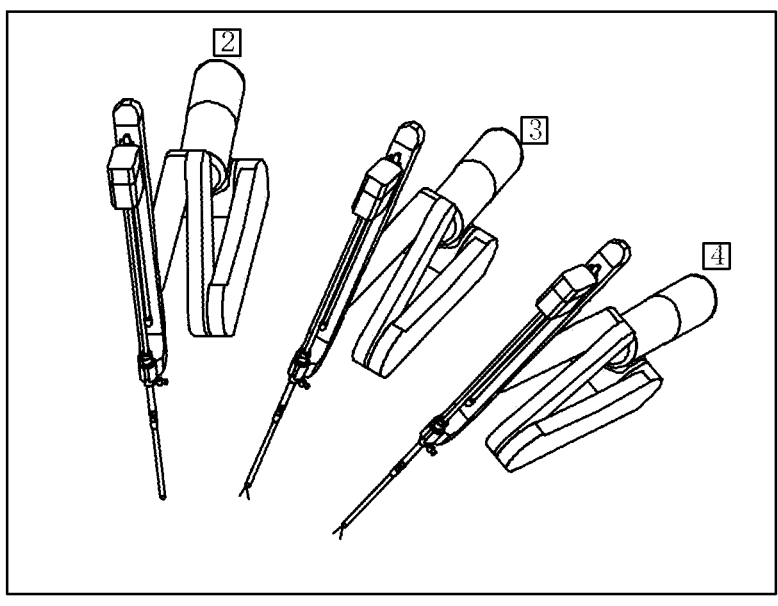
FIG. 10 is a graphic interface of the operation state shown in FIG. 9 according to an embodiment.
Figure 11:
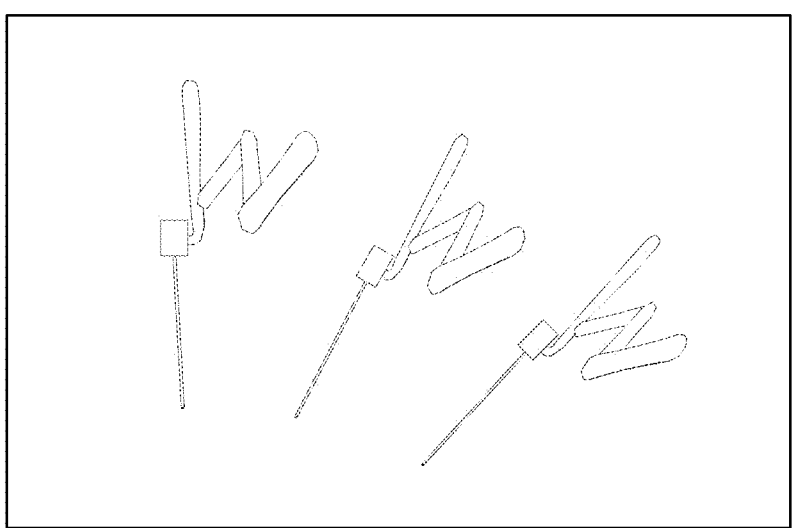
FIG. 11 is a graphic interface of the operation state shown in FIG. 9 according to another embodiment.

In some embodiments, referring to FIG. 9, the surgical robot may include the manipulators 130a, 130b, 130c, and 130d. Each of the manipulators 130b, 130c, and 130d may be provided with an operating arm and may be regarded as a first manipulator. Since the manipulator 130a is not provided with an operating arm and may be regarded as a second manipulator. According to the method of the steps S1-S6, image models of the manipulators 130b, 130c, and 130d are shown in the FIG. 10, each of the models is a computer model corresponding to the first manipulator. In fact, when generating the computer model, it can be generated to substantially represent the structural features of the corresponding manipulator, in other words, the computer model can be simplified to some extent. For example, a simplified computer model basically as shown in FIG. 11 can be generated corresponding to any of the manipulators when no concern is made on the poses and the joint states of a certain manipulator in the reference frame.

In some embodiments, the first manipulators in the first display window can be numbered based on the numbers, such as the numbers 1-4, of the manipulators 130a-130d in the system configuration files, the identifiers. In the embodiment shown in FIG. 9, also referring to FIG. 10, the image models of the manipulators 130b, 130c, and 130d can be numbered, the one corresponding to the manipulator 130b can be numbered 1, the one corresponding to the manipulator 130c can be numbered 2, the one corresponding to the manipulator 130d can be numbered 3. Each number can be displayed at the bottom of the image model of the first manipulator, or displayed at other associated locations that can help the doctor to know the relationship between the external actual manipulator and the image model of the first manipulator displayed on the display, for example, displayed at the proximal end of image model of the manipulator shown in FIG. 10.

Figure 12:
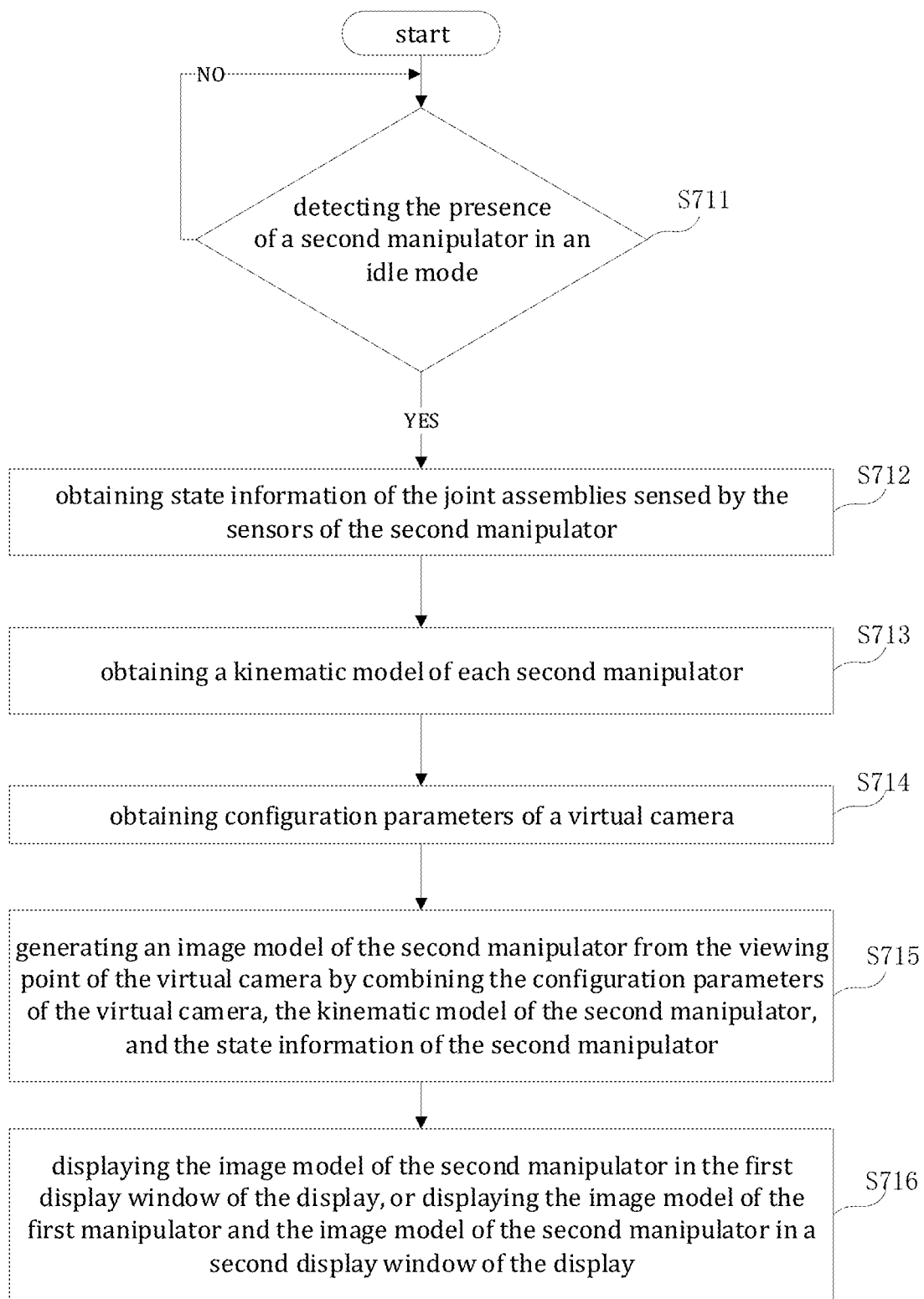
FIG. 12 is a flow diagram of a graphical display method of a surgical robot according to an embodiment of the present disclosure.

In some embodiments, referring to FIG. 12, the graphical display method also may include the following steps:

Step S711, detecting the presence of a second manipulator from a plurality of manipulators, which is in an idle mode.

Proceed to step S712 if the presence of the second manipulator is detected in step S711. Otherwise, continue with step S711.

Step S712, obtaining the state information of the joint assemblies sensed by the sensors of the second manipulator.

Step S713, obtaining a kinematic model of the second manipulator based on the state information of the second manipulator.

The kinematic model of the second manipulator and the kinematic model of the first manipulator can be in a same reference frame directly or through transformation.

Step S714, generating an image model of the second manipulator from the viewing point of the virtual camera by combining the configuration parameters of the virtual camera and the kinematic model of the second manipulator.

Step S715, displaying the image model of the second manipulator in the first display window of the display, or displaying the image model of the first manipulator and the image model of the second manipulator in a second display window of the display.

Figure 13:
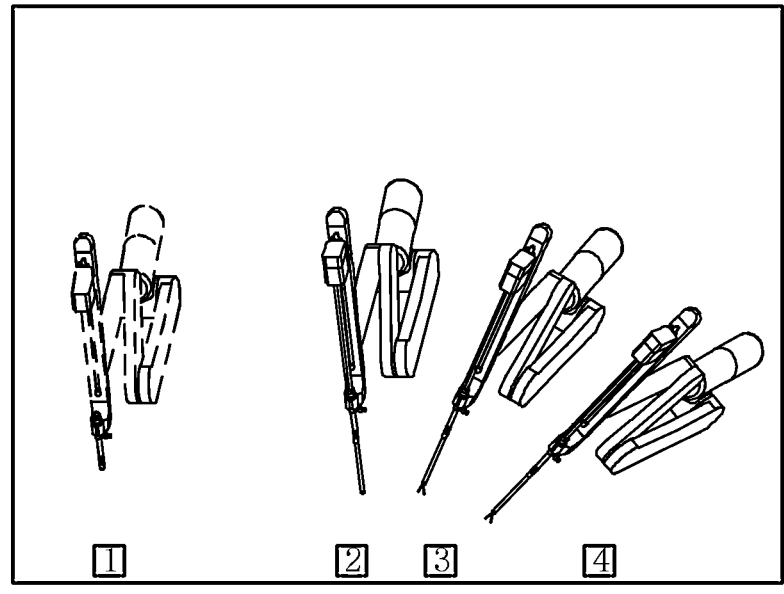
FIG. 13 to FIG. 15 are graphic interfaces of the operation state shown in FIG. 9 according to different embodiments.
Figure 14:
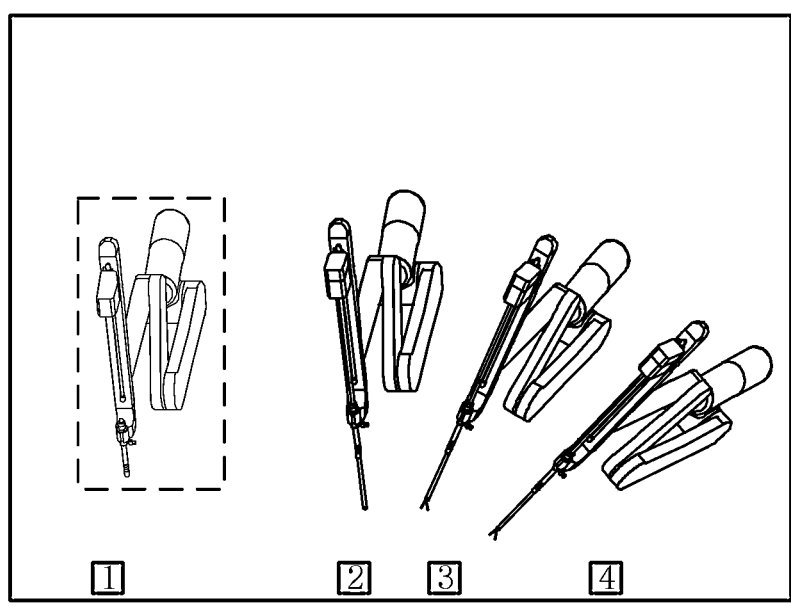

In step S715, referring to FIG. 13 and FIG. 14, the image model of the second manipulator is displayed in the first display window, that is, the image models of the first manipulator and of the second manipulator are simultaneously displayed in the first display window.

Figure 15:
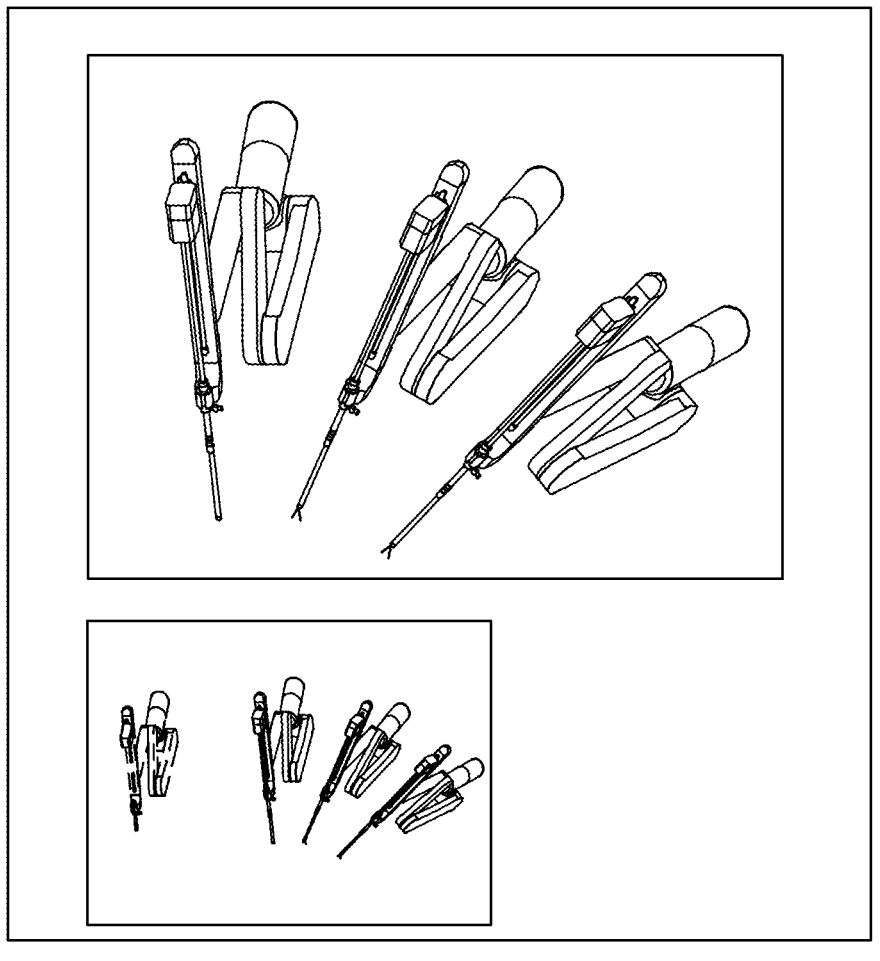

In step S715, referring to FIG. 15, the image model of the second manipulator is displayed in the second display window, and the image models of the first manipulator and of the second manipulator are simultaneously displayed in the second display window. Both of the two methods can show the doctor the poses between all manipulators. The sizes of the first display window and the second display window may be the same or different. For example, the size of the first display window may be made larger to serve as a main auxiliary display window and the second display window serves as a secondary auxiliary display window. For example, the contents displayed in the first display window and in the second display window can be exchanged according to an operating instruction. and the contents displayed in each display window can be scaled proportionally when the sizes of the first display window and the second display window are different.

Generally, the above steps S711-S715 should be executed when the presence of the first manipulator is detected in step S1, since all the manipulators may be regarded as the second manipulators if there is no first manipulator. And since these second manipulators each may be in the idle mode, all of them may be positioned outside the patient's body and kept static, so that it is unnecessarily to display them graphically. The order of steps S1-S6 and steps S711-S715 is not particularly limited herein.

In some embodiments, also referring to FIG. 13-FIG. 15, the image model of the first manipulator and the image model of the second manipulator can be identified in the first display window or the second display window, so as to distinguish the operational modes of the first manipulator and the second manipulator. For example, the colors of the image models of the first manipulator and the second manipulator may be different. For another example, as shown in FIG. 13, different line types may be used to distinguish the image models of the first manipulator and the second manipulator in the first display window, for example, the image model of the first manipulator may be presented in solid lines, and the image model of the second manipulator may be in dotted lines. For another example, as shown in FIG. 14, a box, such as a dashed box, may be put outside of the image model of the second manipulator in the first display window to identify the second manipulator. For another example, as shown in FIG. 15, the image models of the first manipulator and the second manipulator can be identified in the second display window, for instance, the image model of the first manipulator may be presented in solid lines, and the image model of the second manipulator may be in dotted lines. For another example, the image models of the first manipulator and the second manipulator can be identified with numbers in the first display window or in the second display window, for instance the number of the image model of the first manipulator may be presented in solid lines, and the number of the image model of the second manipulator may be in dotted lines.

By providing the image model of the second manipulator in the first display window or in the second display window, the above steps S711-S715 can help the doctor to observe the poses of all the manipulators entirely or comprehensively. On an aspect, these steps can help to avoid the collisions between any two manipulators by knowing the poses of all the manipulators.

In some embodiments, the step S714 may be executed after determining the possibility of collisions between the first manipulator and the second manipulator. This is because the doctor does not have to or need to observe the image model of the second manipulator when it is determined that there is no possibility of collisions between the first manipulator and the second manipulator. Therefore, the first display window can be more concise and no useless information will be introduced to disturb the doctor's observation, by displaying the image model of the first manipulator and not displaying the image model of the second manipulator.

Figure 16:
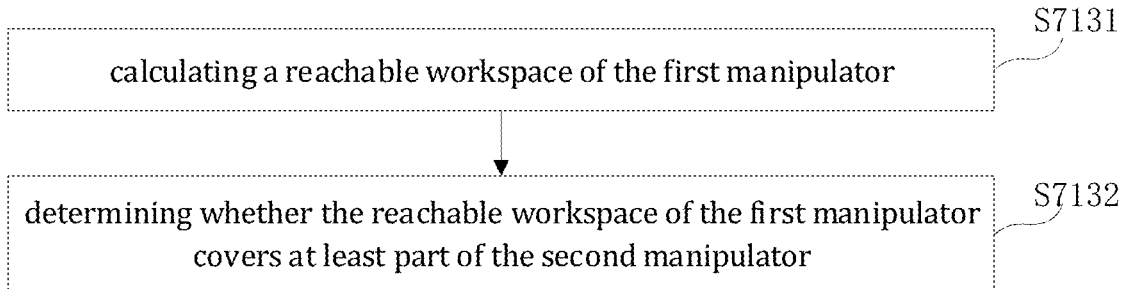
FIG. 16 to FIG. 17 are flow diagrams of the graphical display method of the surgical robot according to different embodiments of the present disclosure.

For example, the possibility of collisions between the first manipulator and the second manipulator can be determined by such a detecting method as shown in FIG. 16, the method includes:

Step S7131, calculating a reachable workspace of the first manipulator.

For example, the reachable workspace can be calculated by combining the link parameters of the first manipulator, the range of motion of each joint assembly of the first manipulator and using the forward kinematics.

Step S7132, determining whether the reachable workspace of the first manipulator covers at least part of the second manipulator.

In Step S7132, determining whether the reachable workspace of the first manipulator covers at least part of the second manipulator can be realized by: building a geometric model by combining the kinematic model and the structural features of the second manipulator, obtaining a point set of external information by discretizing the geometric model of the second manipulator, and further determining whether the reachable workspace of the first manipulator covers at least part of the point set of external information of the second manipulator (for example by calculating the intersection).

Proceed to step S714 if the reachable workspace of the first manipulator covers at least part of the second manipulator, i.e., the possibility of collisions between the first manipulator and the second manipulator is determined in step S7132. Otherwise, continue with step S7131, as the origin of the first manipulator may be changed subsequently and there may be possibility of collisions between the first manipulator and the second manipulator at other times.

In some embodiments, it is also possible to generate an image model of the reachable workspace of the first manipulator from the viewing point of the virtual camera by combining the configuration parameters of the virtual camera and the reachable workspace of the first manipulator in step S7131, i.e., on the basis of the calculation of the reachable workspace of the first manipulator, and then to display the image model of the reachable workspace in the first display window or in the second display window. For example, the image model of the reachable workspace may be a projective model or a computer model of the reachable workspace. From the viewing point of the virtual camera, the image model of the reachable workspace may be presented like a closed figure.

For example, the origin of the image model of the reachable workspace may be coincident with the motion center of the first manipulator. For another example, the origin of the image model of the reachable workspace may be on the axis of the joint assembly at the proximal end of the first manipulator. By displaying the image model of the reachable workspace in the first display window or in the second display window, an indication or a reference on the range of motion of the first manipulator can be provided to the doctor, which may help to avoid the collisions between the first manipulators, and/or between the first manipulator and the second manipulator.

In some embodiments, at least one level of safe motion space can be set in the reachable workspace of the first manipulator, more particularly, the safe motion space can be defined based on the range of motion of each joint assembly of the first manipulator. An image model of the safe motion space from the viewing point of the virtual camera can be generated by combining the configuration parameters of the virtual camera and the safe motion space of the first manipulator, and the image model of the safe motion space can be displayed in the first display window or in the second display window. By displaying the image model of the safe motion space in the first display window or in the second display window, an indication or a reference of a recommended range of motion of the first manipulator can be provided to the doctor more clearly.

In addition, when the image model of the first manipulator moves over the image model of the safe motion space to the image model of the reachable workspace, the image model of the first manipulator, the image model of the safe motion space and/or the image model of the reachable space can be identified in the first display window or in the second display window to remind the doctor to pay attention. For example, reminders can be realized by make at least one of the above image models to flash or to change color.

In case of two or above levels of safe motion spaces, the image model of the first manipulator can be identified differently, such as in different colors or line types, and etc., when the image model of the first manipulator moves to different safe motion space in response to the movement of the first manipulator.

In some embodiments, any image model of the manipulators can be hidden or displayed in the first display window or in the second display window according to an instruction. For example, the image model of the first manipulator can be hidden or displayed. For example, the image model of the second manipulator can be hidden or displayed. For example, any joint assembly in the image model of the first manipulator or the second manipulator can be hidden or displayed. For another example, at least one of the links, the joint assemblies, and the end effector in the image model of the operating arm can be hidden or displayed. In one aspect, the above enables the observation on the poses of the manipulator, which would be otherwise difficult to be observed, by hiding the image model of a corresponding manipulator, when some poses of all the displayed image models of the manipulators overlap with each other from the viewing point of the current virtual camera and affect the doctor's observation on the manipulators. In another aspect, the above is helpful to provide a concise auxiliary view to the doctor.

In some embodiments, the graphical display method mentioned above may further include:

Performing identification on at least part of an image model of a third manipulator in the manipulators in the first display window or in the second display window when the third manipulator reaches a threshold of an event.

The third manipulator may generally refer to a type of manipulator, and should not be understood as only referring to a specific manipulator. The third manipulator may be from the first manipulator and/or the second manipulator mentioned above. The threshold may be a warning threshold, the event may be a situation to be avoided.

Figure 17:
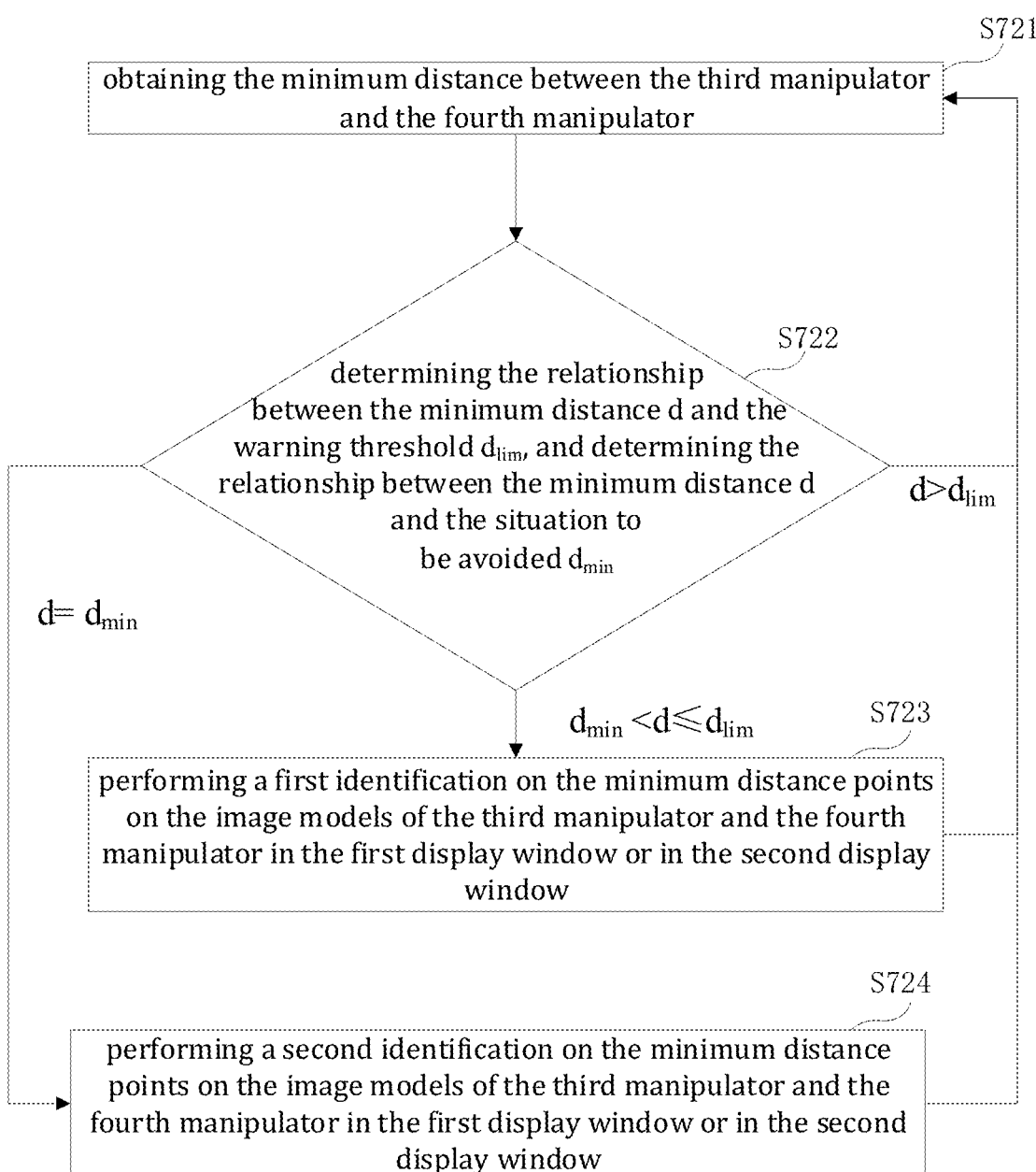

In some specific embodiments, the warning threshold is based on the distance between the third manipulator and a fourth manipulator from the manipulators, for example, the warning threshold can be a value. The situation to be avoided can be the collision between the third manipulator and the fourth manipulator, for example, the situation to be avoided can be a value. The fourth manipulator may generally refer to a type of manipulator, and should not be understood as only referring to a specific manipulator. The fourth manipulator may be from the first manipulator and/or the second manipulator. For example, as shown in FIG. 17, the method can be realized with the following steps:

Step S721, obtaining the minimum distance between the third manipulator and the fourth manipulator.

The step S721 may be executed in real time.

Step S722, determining the relationship between the minimum distance and the warning threshold and the situation to be avoided.

Each of the warning threshold and the situation to be avoided may be represented with a value. When the situation to be avoided is a collision between the third manipulator and the fourth manipulator, the value $d_{lim}$ representing the warning threshold should be larger than the value $d_{min}$ representing the situation to be avoided, that is $d_{lim} > d_{min}$, where the value d represents the minimum distance between the third manipulator and the fourth manipulator. In some embodiments, $d_{min}=0$ represents that the collision has occurred.

Proceed to step S721 if $d > d_{lim}$ in step S722, that is, the minimum distance does not reach the warning threshold. Proceed to step S723 if $d_{min} < d \leq d_{lim}$, that is, the minimum distance has reached the warning threshold but not reached to the situation to be avoided. Proceed to step S724 if $d=d_{min}$, that is, the minimum distance has exceeded the warning threshold and reached to the situation to be avoided.

Step S723, performing a first identification on the minimum distance points on the image models of the third manipulator and the fourth manipulator in the first display window or in the second display window.

Figure 18:
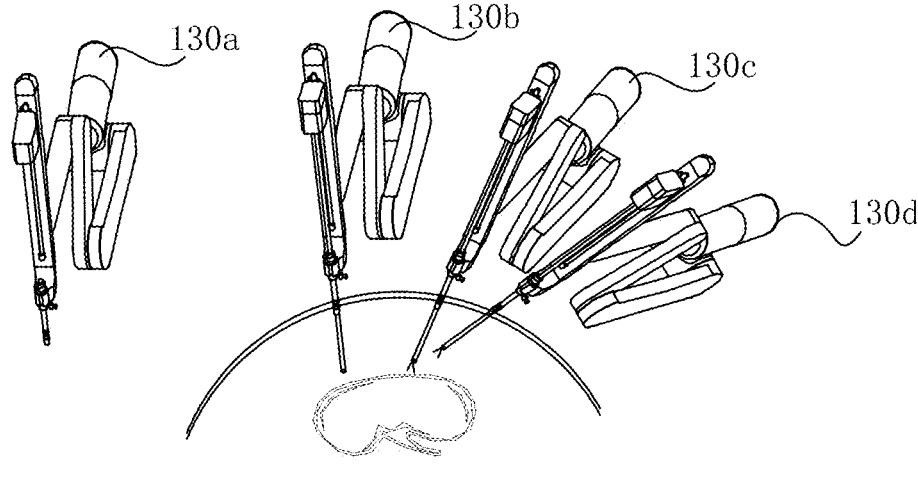
FIG. 18 is a partial schematic diagram of the operation state of the surgical robot according to an embodiment of the present disclosure.
Figure 19:
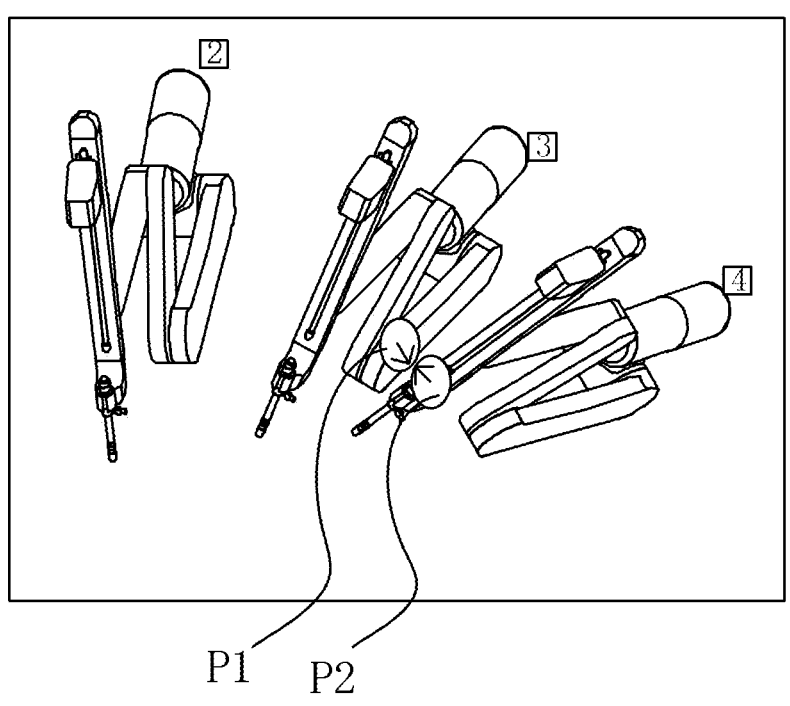

As shown in FIG. 18, the minimum distance between the manipulator 130c and the manipulator 130d has reached the warning threshold, then in step S723, the minimum distance points P1, P2 in the image models of the third manipulator and the fourth manipulator may be identified with color or a graphic frame such as a circle, as shown in FIG. 19. When a redetected minimum distance does not reach the warning threshold, the identifiers on the minimum distance points in the image models of the third manipulator and the fourth manipulator may be eliminated from the first display window or the second display window, as shown in FIG. 10. Proceed to step S724, i.e., perform a second identification if the redetected minimum distance has reached the situation to be avoided.

In addition, in the process of performing the first identification, i.e., when the condition d is satisfied, the first identifier may be changed with the gradually decreasing or increasing minimum distance. For example, the color may be changed gradually, to be different from the color when $d=d_{lim}$. For example, the first identifier may be made to flash, but differently from when $d=d_{min}$.

Step S724, performing a second identification on the minimum distance points on the image models of the third manipulator and the fourth manipulator in the first display window or in the second display window.

The first identification may be different from the second identification. In step S724, for example, the identifier of the minimum distance points P1, P2 in the image models of the third manipulator and the fourth manipulator may be enhanced, for instance the color be deepened. For example, the identifier of the minimum distance points P1, P2 in the image models of the third manipulator and the fourth manipulator may flash. For example, the type of the identifier of the minimum distance points P1, P2 in the image models of the third manipulator and the fourth manipulator may be changed, for instance the type of the graphic frame be changed, as shown in FIG. 20. The solid circle shown in FIG. 19 is replaced by the dotted circle shown in FIG. 20. Proceed to step S723, i.e., perform a first identification when the redetected minimum distance has reached the warning threshold but not reached the situation to be avoided.

Steps S721-S724 can help the doctor to know the collision position between the manipulators.

More particularly, as shown in FIG. 21, the step S721 mentioned above may be realized with the following steps:

Step S7211, building the corresponding geometric models of the third manipulator and of the fourth manipulator based on the respective kinematic models and the structural features of the third manipulator and of the fourth manipulator.

In step S7211, it is generally possible to use a slightly lager basic geometry to replace the actual model to perform the interference analysis, so as to improve the detection efficiency. The respective geometric models of the third manipulator and the fourth manipulator can be simplified to be a sphere, a cylinder, a cuboid, a convex polyhedron, or a combination of two or more thereof.

Step S7212, obtaining the respective point sets of external information of the third manipulator and the fourth manipulator in the reference frame by discretizing the respective geometric models of the third manipulator and the third manipulator.

In step S7212, the point sets of external information of the third manipulator and the fourth manipulator can be obtained by performing datafication to the respective geometric models of the third manipulator and the fourth manipulator.

Step S7213, determining the minimum distance between the third manipulator and the fourth manipulator based on the respective point sets of external information of the third manipulator and the fourth manipulator.

In step S7213, the minimum distance between the third manipulator and the fourth manipulator can be determined by using a distance tracking method. More particularly, the minimum distance between the third manipulator and the fourth manipulator can be determined from the respective point sets of external information of the third manipulator and the fourth manipulator by using a traversal algorithm.

More particularly, as shown in FIG. 22, the step S723 mentioned above maybe realized with the following steps:

Step S7231, determining the minimum distance points in the image models of the third manipulator and the fourth manipulator, which corresponds to the minimum distance between the third manipulator and the fourth manipulator.

Step S7232, performing a first identification on the minimum distance points on the image models of the third manipulator and the fourth manipulator.

In some embodiments, as shown in FIG. 23, when the minimum distance reaches the warning threshold, the graphical display method may further include the following steps:

Step S7233, determining a direction of collision in the reference frame based on the positions of the minimum distance points on the image models of the third manipulator and the fourth manipulator.

Step S7234, performing identification on the direction of the collision between the third manipulator and the fourth manipulator in the first display window or in the second display window.

Visual feedback can be provided to the doctor to avoid the collision by identifying the minimum distance points and the direction of collision between the third manipulator and the fourth manipulator, for example, the direction of collision can be identified by using an arrow vector.

The handle of the master control console can be a mechanical handle. In some embodiments, as shown in FIG. 24, regarding the situation of the step S723, that is, when the minimum distance has reached the warning threshold but not reached the situation to be avoided, the following steps are included:

Step S7233, determining the direction of collision based on the positions of the minimum distance points on the image models of the third manipulator and the fourth manipulator in the reference frame.

Step S7235, generating a resistance for preventing the mechanical handle from moving in an association direction based on the direction of collision.

So that a force feedback can be provided to the doctor to avoid the collision when the manipulators tend to collide.

In particular, the mechanical handle may include a plurality of joint assemblies, sensors and drive motors, the sensors may be coupled to the controller and used for sensing each of the joint assemblies, the drive motors may be coupled to the controller and used for driving each of the joint assemblies to move. Generating the resistance for preventing the mechanical handle from moving in the association direction based on the direction of collision is specifically: generating a reverse torque by the drive motor in the association direction based on the resistance.

When the minimum distance is between the warning threshold and the situation to be avoided, for example, the magnitude of the reverse torque can be constant; for another example, the magnitude of the reverse torque can be negatively correlated with the minimum distance. When the magnitude of the reverse torque is negatively correlated with the minimum distance, more particularly, the reverse torque is increased with the gradual decreasing of the minimum distance to generate a larger resistance, and the reverse torque is decreased with the gradual increasing of the minimum distance to generate a smaller resistance. For example, the change of the reverse torque may be linear. For example, the change of the reverse torque may be non-linear, such as stepped. When the minimum distance has reached the situation to be avoided, at a minimum, the generated reverse torque may at least completely resist the mechanical handle from moving in the direction of collision. In some embodiments, it is possible to detect the force or torque applied by the doctor through the force sensor of each joint assembly of the mechanical handle, and to generate the reverse torque based on the force or the torque applied by the doctor, which reverse torque can at least counteract the force applied by the doctor. In some embodiments, it is also possible to generate a large enough force directly and in a sudden, to prevent a general doctor from moving the mechanical handle in the direction of collision.

In some embodiments, the warning threshold may be based on the range of motion of at least one joint assembly of the third manipulator. The situation to be avoided may be the limitation of the range of motion of the at least one joint assembly of the third manipulator. Similarly, it is possible to identify at least the relevant joint assemblies in the image model of the third manipulator in the first display window or in the second display window when the third manipulator has reached the warning threshold. In addition, it is also possible to generate a resistance at the mechanical handle to prevent the third manipulator from moving beyond the warning threshold to the situation to be avoided. The resistance may be also achieved by generating the reverse torque by the associated drive motors.

In some embodiments, the graphic display method mentioned above may be further include:

Performing identification on the image model of the third manipulator in the first display window or in the second display window when a movement of the third manipulator from the first manipulators is detected. More particularly, whether the first manipulator has moved can be determined by the sensor sensing whether the state of each joint assembly of the first manipulator has changed. That the state has changed represents that the first manipulator has moved.

Figure 25:
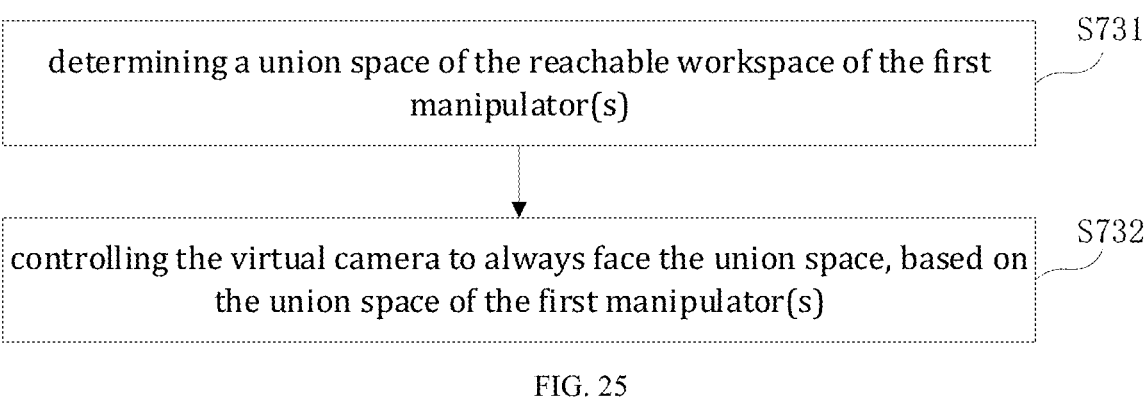

In some embodiments, as shown in FIG. 25, the graphic display method may further include:

Step S731, determining a union space of the reachable workspaces of the first manipulators.

Step S732, controlling the virtual camera to always face the union space, based on the union space of the first manipulators.

For example, it is possible to only allow the pose of the virtual camera to be outside of the union space to facilitate the virtual camera to observe the space entirely. For another example, when the union space needs to be observed locally, the pose of the virtual camera may be allowed to be positioned inside the union space. When there is only one manipulator, the union space is same to the reachable workspace of the manipulator. When there are two or more manipulators, the union space is a space corresponding to the union of the respective reachable workspaces of the manipulators. The reachable workspace of each manipulator in the reference frame can be determined according to the kinematic model of the manipulator, and stored in the memory mentioned above to be called directly. Of course, the reachable workspace of each manipulator in the reference frame can also be recalculated once or more according to the kinematic model of the manipulator every time the surgical robot is started.

To facilitate the observation on the image model of the first manipulator to know the pose of the first manipulator, the field of view of the virtual camera may cover at least part of the union space, so as to facilitate future adjustment on the virtual camera.

In some embodiments, an icon of the virtual camera can be displayed in the first display window or in the second display window, so as to facilitate setting the configuration parameters of the virtual camera.

Figure 26:
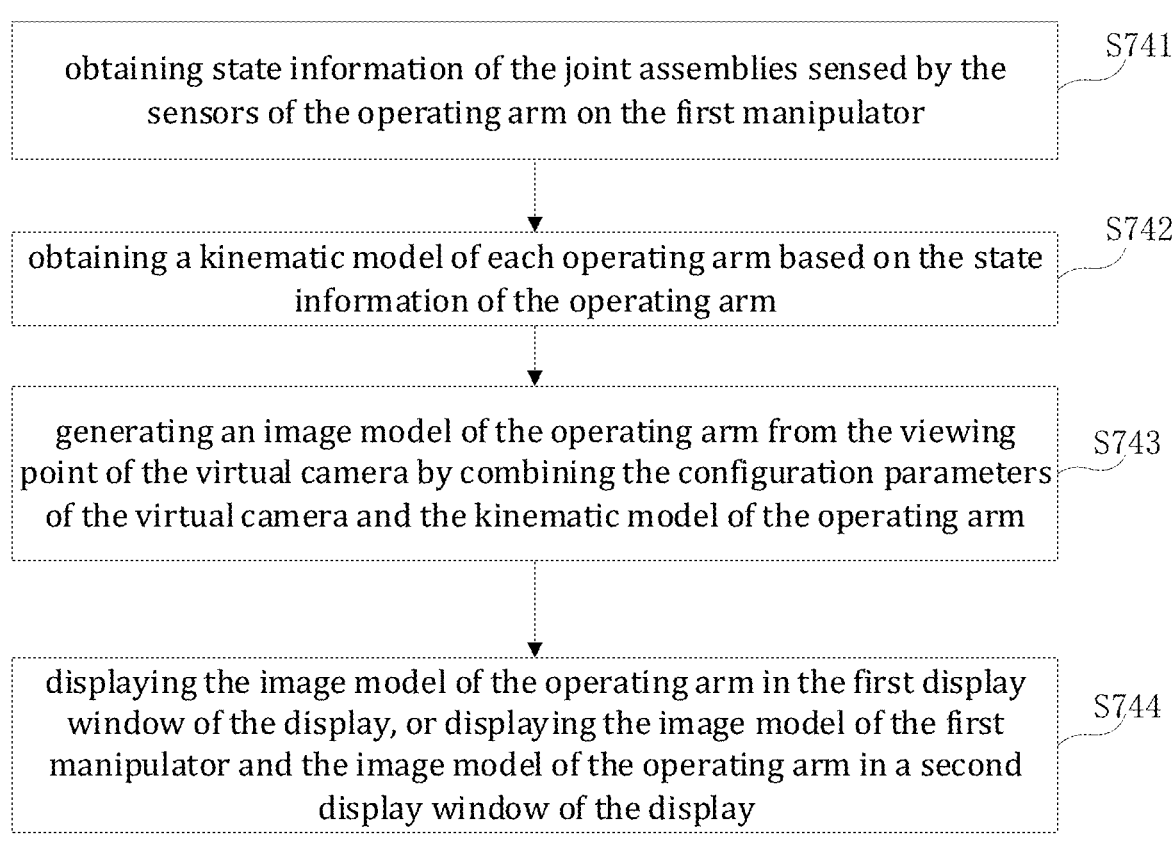

In some embodiments, as shown in FIG. 26, the graphic display method mentioned above may further include:

Step S741, obtaining state information of the joint assemblies sensed by the sensors of the operating arm on the first manipulator.

Step S742, obtaining a kinematic model of the operating arm based on the state information of the operating arm.

Step S743, generating an image model of the operating arm from the viewing point of the virtual camera by combining the configuration parameters of the virtual camera and the kinematic model of the operating arm.

Step S744, displaying the image model of the operating arm in the first display window of the display, or displaying the image models of the first manipulator and its operating arm in the second display window of the operating arm.

Generally, the steps S741-S744 are executed on the basis that the presence of the first manipulator is detected in step S1, since all the manipulators are regarded as the second manipulators if there is no first manipulator, these second manipulators are in the idle mode, all of them may be positioned outside the patient's body and kept static. They are generally provided with no operating arm, but it may be unnecessary to display them graphically even if they are provided with an operating arm. The order of the steps S1-S6 and the steps S7141-S744 is not particularly limited herein.

The above steps S741-S744 enable an overall observation on the manipulator assembly including the first manipulator and the operating arm mounted thereon, to facilitate the doctor to know the pose of the entire manipulator assembly, so as to pay attention in advance to avoid the collision of any part of the manipulator assembly.

In some embodiments, it is possible to hide or display an image model of any part of the first manipulator assembly including the first manipulator and the operating arm mounted thereon in the first display window or in the second display window according to an instruction. For example, the image model of the first manipulator can be hidden or displayed. For example, the image model of the operating arm can be hidden or displayed. For example, any joint assembly in the image model of the first manipulator or of the second manipulator can be hidden or displayed. For another example, at least one of the links, the joint assemblies, and the end effector in the image model of the operating arm can be hidden or displayed. In one aspect, the above enables the observation on the poses of the manipulator assembly, which would be otherwise difficult to be observed, by hiding the image model of a corresponding manipulator assembly, when some poses of all the displayed image models of the manipulator assemblies overlap with each other from the viewing point of the current virtual camera and affect the doctor's observation on the manipulator assembly. In another aspect, the above is helpful to provide a concise auxiliary view to the doctor.

Figure 27:
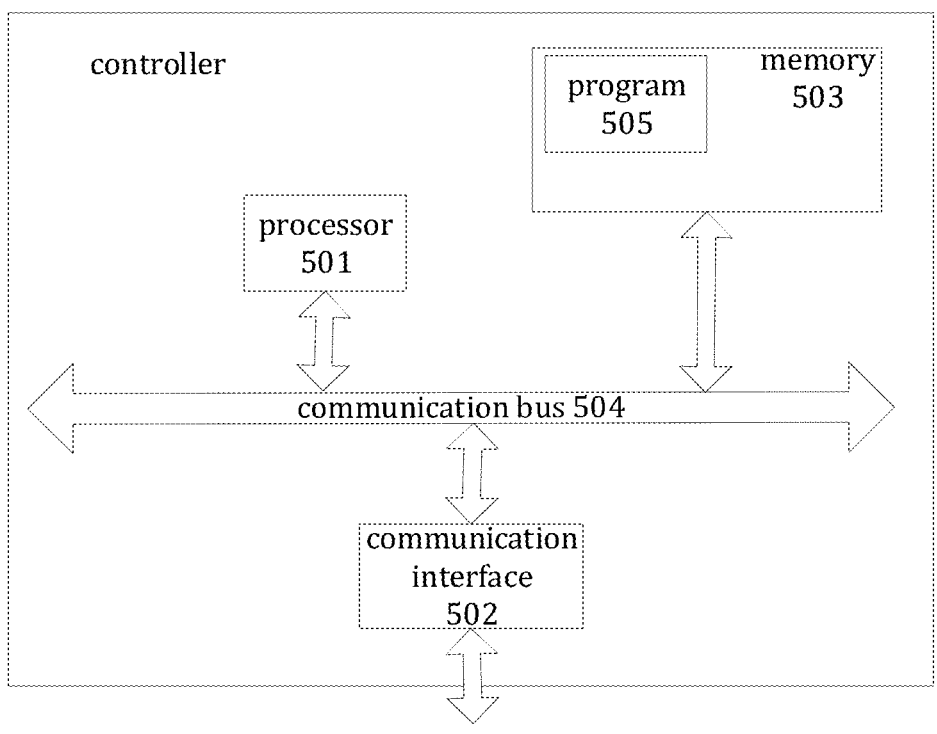
FIG. 27 is a schematic structure diagram of a graphical control device of a surgical robot according to an embodiment of the present disclosure.

In some embodiments, as shown in FIG. 27, the graphical control device can include: a processor 501, a communication interface 502, a memory 503, and a communication bus 504.

The processor 501, the communication interface 502, and the memory 503 can communicate with each other through the communication bus 504.

The communication interface 502 is configured to communicate with network elements of other devices such as various sensors or motors or solenoid valves or other clients or servers, etc.

The processor 501 is configured to execute the program 505, and may specifically execute the corresponding steps in the embodiments of the method mentioned above.

Specifically, the program 505 may include program codes that includes computer operation instructions.

The processor 501 may be a central processing unit (CPU), or a specific integrated circuit ASIC (Application Specific Integrated Circuit), or be one or more integrated circuits configured to implement the embodiments of the present disclosure, or be a GPU (Graphics Processing Unit). The one or more processors of the control device may be the same type of processors, such as one or more CPU, or one or more GPU. The one or more processors of the control device also may be different types of processors, such as one or more CPU, and one or more GPU.

The memory 503 is configured to store the program 505. The memory 503 may include a high-speed RAM memory, or may further include a non-volatile memory, such as at least one magnetic disk memory.

The program 505 may be specifically configured to make the processor 501 to execute the following operations:

Obtaining state information of the joint assemblies sensed by the sensors of the first manipulator when a first manipulator is detected to be in an operational modes; obtaining a kinematic model of the first manipulator; obtaining configuration parameters of a virtual camera; generating an image model of the first manipulator from the viewing point of the virtual camera by combining the configuration parameters of the virtual camera, the kinematic model of the first manipulator and its state information; displaying the image model of the first manipulator in a first display window of the display.

The various technical features of the above-described embodiments may be combined in any combination, so that the description is concise, and all possible combinations of the various technical features in the above-described embodiments are described. However, as long as the combination of these technical features does not conflict, it is to be understood that the scope of the present specification is not to be taken in a limiting sense.

The above-described embodiments have only expressed several embodiments of the present application, which are described in more detail and detail, but are not therefore to be construed as limiting the scope of the present application. It should be noted that variations and modifications may be made to one of ordinary skill in the art without departing from the spirit of the present application, all of which fall within the scope of the present application. Therefore, the scope of the appended claims should be accorded the broadest interpretation so as to encompass all such modifications and similar arrangements.

What is claimed is:

1. A surgical robot, comprising:

a display;

at least two manipulators, each comprising a plurality of joint assemblies, each joint assembly being provided with a sensor configured to sense a state of the joint assembly, each manipulator being configured to be detachably connected to an operating arm, and each manipulator being positioned outside a patient's body and a distal end of the operating arm inserting into the patient's body with a puncture device mounted to the manipulator during a surgical process; and a controller, coupled to the display and to the sensor, and configured for:

obtaining a kinematic model of the first manipulator and obtaining a kinematic model of the second manipulator, in response to detecting a presence of a first manipulator which is in an operational mode and a presence of a second manipulator which is in an idle mode, and determining a possibility of collision between the first manipulator and the second manipulator;

obtaining configuration parameters of a virtual camera;

generating an image model of the first manipulator from a viewing point of the virtual camera by combining the configuration parameters of the virtual camera, the kinematic model of the first manipulator, and the state information of the plurality of joint assemblies of the first manipulator, and generating an image model of the second manipulator from the viewing point of the virtual camera by combining the configuration parameters of the virtual camera, the kinematic model of the second manipulator and the state information of the plurality of joint assemblies of the second manipulator; and displaying the image model of the first manipulator and the image model of the second manipulator in a first display window of the display; or displaying the image model of the first manipulator in the first display window of the display, and displaying the image model of the second manipulator in the second display window of the display.

2. The surgical robot according to claim 1, wherein, the controller is configured for:

detecting among the at least two manipulators a presence of a second manipulator which is in an idle mode;

obtaining state information of the plurality of joint assemblies sensed by the sensors of the second manipulator in response to detecting the presence of the second manipulator;

obtaining a kinematic model of the second manipulator;

generating an image model of the second manipulator from the viewing point of the virtual camera by combining the configuration parameters of the virtual camera, the kinematic model of the second manipulator and the state information of the second manipulator; and displaying the image model of the second manipulator in the first display window of the display, or displaying the image models of the first manipulator and of the second manipulator in a second display window of the display.

3. The surgical robot according to claim 2, wherein, when generating the image model of the second manipulator from the viewing point of the virtual camera by combining the configuration parameters of the virtual camera and the kinematic model of the second manipulator, the controller is configured for:

generating the image model of the second manipulator from the viewing point of the virtual camera by combining the configuration parameters of the virtual camera, the kinematic model of the second manipulator and the state information of the second manipulator after determining a possibility of collision between the first manipulator and the second manipulator.

4. The surgical robot according to claim 1, wherein, the controller is configured for executing following steps to determine whether there is a possibility of collision between the first manipulator and the second manipulator:

calculating a reachable workspace of the first manipulator;

determining whether the reachable workspace of the first manipulator covers at least part of the second manipulator; and determining that there is possibility of collision between the first manipulator and the second manipulator, if it is determined that the reachable workspace of the first manipulator covers at least part of the second manipulator.

5. The surgical robot according to claim 1, wherein, the controller is configured for:

calculating a reachable workspace of the first manipulator;

generating an image model of the reachable workspace of the first manipulator from the viewing point of the virtual camera by combining the configuration parameters of the virtual camera and the reachable workspace of the first manipulator; and displaying the image model of the reachable workspace in the first display window or in the second display window;

wherein an origin of the image model of the reachable workspace is coincident with a motion center of the first manipulator, or, the origin of the image model of the reachable workspace is positioned on an axis of the joint assembly at a proximal end of the first manipulator.

6. The surgical robot according to claim 5, wherein; the first manipulator is configured to comprise a safe motion space within the reachable workspace, the controller is configured for:

generating an image model of the safe motion space of the first manipulator by combining the configuration parameters of the virtual camera and the safe motion space of the first manipulator from the viewing point of the virtual camera;

displaying the image model of the safe motion space in the first display window or in the second display window; and generating an identifier to identify the image model of the first manipulator, the safe motion space, and/or the reachable workspace in the first display window or in the second display window when the image model of the first manipulator is detected to have moved from the image model of the safe motion space to a part of the image model of the reachable workspace other than the safe motion space.

7. The surgical robot according to claim 1, wherein, the controller is configured for:

generating an identifier to identify at least one part of an image model of a third manipulator from the at least two manipulators in the first display window or in the second display window when the third manipulator is detected to have reached a threshold of event, wherein the threshold is a warning threshold, the event is a situation to be avoided.

8. The surgical robot according to claim 7, wherein:

the warning threshold is based on a distance between the third manipulator and a fourth manipulator from the at least two manipulators, the situation to be avoided is a collision between the third manipulator and the fourth manipulator, the controller is configured for:

obtaining a minimum distance between the third manipulator and the fourth manipulator, and determining a relationship between the minimum distance and the warning threshold;

generating a first identifier to identify minimum distance points on the image models of the third manipulator and the fourth manipulator in the first display window or in the second display window when the minimum distance has reached the warning threshold, but not reached a threshold corresponding to the situation to be avoided; and generating a second identifier to identify the minimum distance points on the image models of the one third manipulator and the fourth manipulator in the first display window or in the second display window when the minimum distance has reached the threshold corresponding to the situation to be avoided.

9. The surgical robot according to claim 8, wherein, the controller is configured for:

obtaining the minimum distance between the third manipulator and the fourth manipulator, and determining the relationship between the minimum distance and the warning threshold, which comprises:

building a geometric model of the third manipulator based on a kinematic model and structural features of the third manipulator, and building a geometric model of the fourth manipulator based on a kinematic model and structural features of the fourth manipulator;

obtaining a point set of external information of the third manipulator by discretizing the geometric model of the third manipulator in a reference frame, and obtaining a point set of external information of the fourth manipulator by discretizing the geometric model of the fourth manipulator in the reference frame; and determining the minimum distance between the third manipulator and the fourth manipulator based on the point sets of external information of the third manipulator and of the fourth manipulator; and generating the first identifier to identify the minimum distance points on the image models of the third manipulator and the fourth manipulator in the first display window or in the second display window, which comprises:

determining the minimum distance points corresponding to the minimum distance, and generating the first identifier to identify the minimum distance points on the image models of the third manipulator and the fourth manipulator in the first display window or in the second display window.

10. The surgical robot according to claim 9, wherein, the controller is configured for:

determining a direction of collision based on positions of the minimum distance points on the image models of the third manipulator and the fourth manipulator in the reference frame when the minimum distance has reached to the warning threshold; and generating an identifier to identify the direction of collision between the third manipulator and the fourth manipulator in the first display window or in the second display window.

11. The surgical robot according to claim 9, wherein; the surgical robot comprises a mechanical handle coupled to the controller and configured to control the at least two manipulators to move, the controller is configured for:

generating a resistance to prevent the mechanical handle from moving in an association direction based on the direction of collision.

12. The surgical robot according to claim 11, wherein, the mechanical handle comprises a plurality of joint assemblies and drive motors for actuating each of the plurality of joint assemblies of the mechanical handle to move, each of the drive motors are coupled to the controller, the controller is configured for:

causing a drive motor in the association direction to generate a reverse torque based on the resistance, wherein magnitude of the reverse torque is set to be negatively correlated with the minimum distance when the minimum distance is between the warning threshold and the threshold corresponding to the situation to be avoided.

13. The surgical robot according to claim 7, wherein:

the warning threshold is based on a range of motion of at least one joint assembly of the third manipulator, the situation to be avoided is a limitation of the range of motion of the at least one joint assembly of the third manipulator.

14. The surgical robot according to claim 2, wherein, the controller is configured for:

performing identification on the first manipulator in the first display window or in the second display window; and generating an identifier to identify an image model of a third manipulator from the first manipulator in the first display window or in the second display window when a movement of the third manipulator is detected;

wherein the image model of the first manipulator is a computer model or a projective model presenting structural features of the first manipulator.

15. The surgical robot according to claim 1, wherein, the surgical robot comprises an operating arm detachably connected to the first manipulator, the operating arm comprises a plurality of joint assemblies and sensors configured to sense the state of the plurality of joint assemblies of the operating arm; the controller is configured for:

obtaining state information of the joint assemblies sensed by the sensors of the operating arm on the first manipulator;

obtaining a kinematic model of the operating arm based on the state information of the operating arm;

generating an image model of the operating arm from the viewing point of the virtual camera by combining the configuration parameters of the virtual camera and the kinematic model of the operating arm; and displaying the image model of the operating arm in the first display window of the display, or displaying the image model of the first manipulator and the image model of the operating arm in a second display window of the display.

16. The surgical robot according to claim 1, wherein:

the surgical robot comprises an input device coupled to the controller and configured to set the configuration parameters of the virtual camera, the configuration parameters comprise a pose of the virtual camera in a reference frame, a virtual focal length of the virtual camera, and/or a virtual aperture of the virtual camera.

17. The surgical robot according to claim 1, wherein; the controller is configured for:

calculating a reachable workspace of the first manipulator;

determining a union space of the reachable workspace of the first manipulator; and controlling the virtual camera to keep facing the union space based on the union space.

18. The surgical robot according to claim 17, wherein, the controller is configured for:

determining a center of the union space while determining the union space of the reachable workspace of the first manipulator; and controlling an optical axis of the virtual camera to keep intersecting on the center of the union space based on the center of union space while controlling the virtual camera to keep facing the union space based on the union space.

19. A graphical display method of a surgical robot, wherein the surgical robot comprises:

a display; and at least two manipulators, each comprising a plurality of joint assemblies, each joint assembly being provided with a sensor configured to sense a state of the joint assembly, each manipulator being configured to be detachably connected to an operating arm, and each manipulator being positioned outside a patient's body and a distal end of the operating arm inserting into the patient's body with a puncture device mounted to the manipulator during a surgical process;

the graphical display method comprises:

obtaining a kinematic model of the first manipulator;

obtaining a kinematic model of the first manipulator and obtaining a kinematic model of the second manipulator, in response to detecting a presence of a first manipulator which is in an operational mode and a presence of a second manipulator which is in an idle mode, and determining a possibility of collision between the first manipulator and the second manipulator;

obtaining configuration parameters of a virtual camera;

generating an image model of the first manipulator from a viewing point of the virtual camera by combining the configuration parameters of the virtual camera, the kinematic model of the first manipulator, and the state information of the plurality of joint assemblies of the first manipulator, and generating an image model of the second manipulator from the viewing point of the virtual camera by combining the configuration parameters of the virtual camera, the kinematic model of the second manipulator and the state information of the plurality of joint assemblies of the second manipulator; and displaying the image model of the first manipulator and the image model of the second manipulator in a first display window of the display; or displaying the image model of the first manipulator in the first display window of the display, and displaying the image model of the second manipulator in the second display window of the display.

20. A graphical control device of a surgical robot, wherein the graphical control device comprises:

a memory, configured for storing a computer program; and a processing unit, configured for loading and executing the computer program;

wherein the computer program is configured for being loaded and executed by the processing unit to implement steps in the graphical display method according to claim 19.

* * * * *